United States Patent
Rawson et al.

(10) Patent No.: US 9,085,517 B2
(45) Date of Patent: Jul. 21, 2015

(54) SULFONAMIDE DERIVATIVES

(71) Applicant: Pfizer Limited, Sandwich, Kent (GB)

(72) Inventors: David James Rawson, Sandwich (GB); Robert Ian Storer, Great Abington (GB); Nigel Alan Swain, Great Abington (GB)

(73) Assignee: Pfizer Limited, Sandwich, Kent (GB)

( * ) Notice: Subject to any disclaimer, the term of this patent is extended or adjusted under 35 U.S.C. 154(b) by 0 days.

(21) Appl. No.: 14/358,494

(22) PCT Filed: Dec. 6, 2012

(86) PCT No.: PCT/IB2012/057035
§ 371 (c)(1),
(2) Date: May 15, 2014

(87) PCT Pub. No.: WO2013/088315
PCT Pub. Date: Jun. 20, 2013

(65) Prior Publication Data
US 2014/0315879 A1 Oct. 23, 2014

Related U.S. Application Data

(60) Provisional application No. 61/576,005, filed on Dec. 15, 2011.

(51) Int. Cl.
| | | |
|---|---|---|
| C07D 307/00 | (2006.01) | |
| A61K 31/00 | (2006.01) | |
| C07C 307/06 | (2006.01) | |
| C07D 213/89 | (2006.01) | |
| C07D 401/12 | (2006.01) | |
| C07D 205/04 | (2006.01) | |
| C07D 213/64 | (2006.01) | |
| C07D 213/65 | (2006.01) | |
| C07D 213/69 | (2006.01) | |
| A61K 31/18 | (2006.01) | |
| A61K 31/44 | (2006.01) | |
| A61K 31/4427 | (2006.01) | |

(52) U.S. Cl.
CPC .............. *C07C 307/06* (2013.01); *A61K 31/18* (2013.01); *A61K 31/44* (2013.01); *A61K 31/4427* (2013.01); *C07D 205/04* (2013.01); *C07D 213/64* (2013.01); *C07D 213/65* (2013.01); *C07D 213/69* (2013.01); *C07D 213/89* (2013.01); *C07D 401/12* (2013.01); *C07C 2101/02* (2013.01)

(58) Field of Classification Search
None
See application file for complete search history.

(56) References Cited

FOREIGN PATENT DOCUMENTS

| | | |
|---|---|---|
| EP | 2327701 | 6/2011 |
| JP | 5289262 | 11/1993 |
| WO | 9421590 | 9/1994 |
| WO | 9604905 | 2/1996 |
| WO | 9609818 | 4/1996 |
| WO | 0039077 | 7/2000 |
| WO | 02060388 | 8/2002 |
| WO | 2005013914 | 2/2005 |
| WO | 2005020921 | 3/2005 |
| WO | 2006043090 | 4/2006 |
| WO | 2008008234 | 1/2008 |
| WO | 2008047229 | 4/2008 |
| WO | 2008118758 | 10/2008 |
| WO | 2008135826 | 11/2008 |
| WO | 2009012242 | 1/2009 |
| WO | 2009080835 | 7/2009 |
| WO | 2009140342 | 11/2009 |
| WO | 2011070592 | 6/2011 |
| WO | 2011100607 | 8/2011 |
| WO | 2011100614 | 8/2011 |
| WO | 2011127565 | 10/2011 |
| WO | 2011127567 | 10/2011 |
| WO | 2012007869 | 1/2012 |

OTHER PUBLICATIONS

PCT/IB2012/057035 International Search Report and Written Opinion mailed Feb. 26, 2013, 11 pages.

*Primary Examiner* — Heidi Reese
(74) *Attorney, Agent, or Firm* — Richard V. Zanzalari

(57) ABSTRACT

The present invention relates to sulfonamide derivatives, of formula (I):

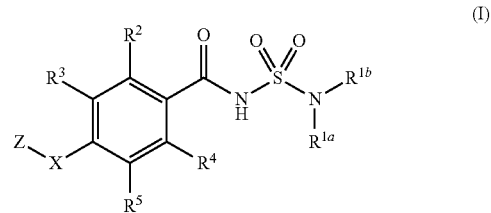

or a pharmaceutically acceptable salts thereof, wherein X, Z, $R^{1a}$, $R^{1b}$, $R^2$, $R^3$, $R^4$ and $R^5$ are as defined in the description, and to their use in medicine, to compositions containing them, to processes for their preparation and to intermediates used in such processes. The compounds of formula (I) are Nav1.7 inhibitors useful in the treatment of a wide range of disorders, particularly pain.

18 Claims, No Drawings

SULFONAMIDE DERIVATIVES

This application is a national stage application under 35 U.S.C. 371 of PCT/IB2012/057035, filed on Dec. 6, 2012, which claims the benefit of U.S. Provisional Patent Application No. 61/576,005, filed on Dec. 15, 2011, the disclosures of which are hereby incorporated by reference in their entirety.

The invention relates to sulfonamide derivatives, to their use in medicine, to compositions containing them, to processes for their preparation and to intermediates used in such processes.

Voltage-gated sodium channels are found in all excitable cells including myocytes of muscle and neurons of the central and peripheral nervous system. In neuronal cells, sodium channels are primarily responsible for generating the rapid upstroke of the action potential. In this manner sodium channels are essential to the initiation and propagation of electrical signals in the nervous system. Proper and appropriate function of sodium channels is therefore necessary for normal function of the neuron. Consequently, aberrant sodium channel function is thought to underlie a variety of medical disorders (see Hubner C A, Jentsch T J, *Hum. Mol. Genet.*, 11(20): 2435-45 (2002) for a general review of inherited ion channel disorders) including epilepsy (Yogeeswari et al., *Curr. Drug Targets*, 5(7): 589-602 (2004)), arrhythmia (Noble D., *Proc. Natl. Acad. Sci. USA*, 99(9): 5755-6 (2002)) myotonia (Cannon, S C, *Kidney Int.* 57(3): 772-9 (2000)), and pain (Wood, J N et al., *J. Neurobiol.*, 61(1): 55-71 (2004)).

There are currently at least nine known members of the family of voltage-gated sodium channel (VGSC) alpha subunits. Names for this family include SCNx, SCNAx, and $Na_vx.x$. The VGSC family has been phylogenetically divided into two subfamilies $Na_v1.x$ (all but SCN6A) and $Na_v2.x$ (SCN6A). The Nav1.x subfamily can be functionally subdivided into two groups, those which are sensitive to blocking by tetrodotoxin (TTX-sensitive or TTX-s) and those which are resistant to blocking by tetrodotoxin (TTX-resistant or TTX-r).

The $Na_v1.7$ (PN1, SCN9A) VGSC is sensitive to blocking by tetrodotoxin and is preferentially expressed in peripheral sympathetic and sensory neurons. The SCN9A gene has been cloned from a number of species, including human, rat, and rabbit and shows ~90% amino acid identity between the human and rat genes (Toledo-Aral et al., *Proc. Natl. Acad. Sci. USA*, 94(4): 1527-1532 (1997)).

An increasing body of evidence suggests that $Na_v1.7$ may play a key role in various pain states, including acute, inflammatory and/or neuropathic pain. Deletion of the SCN9A gene in nociceptive neurons of mice led to a reduction in mechanical and thermal pain thresholds and reduction or abolition of inflammatory pain responses (Nassar et al., *Proc Natl Acad Sci USA*, 101(34): 12706-11 (2004)). In humans, $Na_v1.7$ protein has been shown to accumulate in neuromas, particularly painful neuromas (Kretschmer et al., *Acta. Neurochir. (Wien)*, 144(8): 803-10 (2002)). Gain of function mutations of $Na_v1.7$, both familial and sporadic, have been linked to primary erythermalgia, a disease characterized by burning pain and inflammation of the extremities (Yang et al., *J. Med. Genet.*, 41(3): 171-4 (2004), and paroxysmal extreme pain disorder (Waxman, S G *Neurology.* 7; 69(6): 505-7 (2007)). Congruent with this observation is the report that the non-selective sodium channel blockers lidocaine and mexiletine can provide symptomatic relief in cases of familial erythermalgia (Legroux-Crepel et al., *Ann. Dermatol Venereol.*, 130: 429-433) and carbamazepine is effective in reducing the number and severity of attacks in PEPD (Fertleman et al, *Neuron.;* 52(5):767-74 (2006). Further evidence of the role of Nav1.7 in pain is found in the phenotype of loss of function mutations of the SCN9A gene. Cox and colleagues (*Nature,* 444(7121):894-8 (2006)) were the first to report an association between loss-of-function mutations of SNC9A and congenital indifference to pain (CIP), a rare autosomal recessive disorder characterized by a complete indifference or insensitivity to painful stimuli. Subsequent studies have revealed a number of different mutations that result in a loss of function of the SCN9A gene and the CIP phenotype (Goldberg et al, *Clin Genet.;* 71(4): 311-9 (2007), Ahmad et al, *Hum Mol Genet.* 1; 16(17): 2114-21 (2007)).

Nav 1.7 inhibitors are therefore potentially useful in the treatment of a wide range of disorders, particularly pain, including: acute pain; chronic pain; neuropathic pain; inflammatory pain; visceral pain; nociceptive pain including post-surgical pain; and mixed pain types involving the viscera, gastrointestinal tract, cranial structures, musculoskeletal system, spine, urogenital system, cardiovascular system and CNS, including cancer pain, back and orofacial pain.

Certain inhibitors of voltage gated sodium channels useful in the treatment of pain are known. Thus WO-A-2005/013914 discloses heteroarylamino sulfonylphenyl derivatives, WO-A-2008/118758 aryl sulphonamides and WO-A-2009/012242 N-thiazolyl benzenesulfonamides.

There is, however, an ongoing need to provide new $Na_v1.7$ inhibitors that are good drug candidates.

Preferably compounds are selective Nav1.7 channel inhibitors. That is, preferred compounds show an affinity for the Nav1.7 channel over other Nav channels. In particular, they should show an affinity for the Nav1.7 channel which is greater than their affinity for Nav1.5 channels. Advantageously, compounds should show little or no affinity for the Nav1.5 channel.

Selectivity for the Nav1.7 channel over Nav1.5 may potentially lead to one or more improvements in side-effect profile. Without wishing to be bound by theory, such selectivity is thought to reduce any cardiovascular side effects which may be associated with affinity for the Nav1.5 channel. Preferably compounds demonstrate a selectivity of 10-fold, more preferably 30-fold, most preferably 100-fold, for the Nav 1.7 channel when compared to their selectivity for the Nav1.5 channel whilst maintaining good potency for the Nav1.7 channel.

Furthermore, preferred compounds should have one or more of the following properties: be well absorbed from the gastrointestinal tract; be metabolically stable; have a good metabolic profile, in particular with respect to the toxicity or allergenicity of any metabolites formed; or possess favourable pharmacokinetic properties whilst still retaining their activity profile as Nav1.7 channel inhibitors. They should be non-toxic and demonstrate few side-effects. Ideal drug candidates should exist in a physical form that is stable, non-hygroscopic and easily formulated.

We have now found new sulphonamide Nav1.7 inhibitors.

According to a first aspect of the invention there is provided a compound of formula (I)

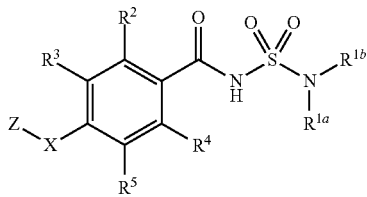

or a pharmaceutically acceptable salt thereof, wherein
X is —OCH$_2$— or —CH$_2$O—;
Z is a group selected from naphthyl, phenyl and Het$^1$, said group being optionally independently substituted by one to three substituents selected from Y$^1$ and Y$^2$;
Y$^1$ and Y$^2$ are independently selected from F; Cl; CN; (C$_1$-C$_8$)alkyl, optionally substituted by (C$_3$-C$_8$)cycloalkyl and/or, valency permitting, by one to eight F; (C$_3$-C$_8$)cycloalkyl, optionally substituted, valency permitting, by one to eight F; NR$^7$R$^8$; (C$_1$-C$_8$)alkyloxy, optionally independently substituted by one to three R$^9$, and/or, valency permitting, by one to eight F; (C$_3$-C$_8$)cycloalkyloxy, optionally independently substituted, valency permitting, by one to eight F and/or by one to three R$^{10}$, and further optionally fused to a phenyl ring; phenyl, optionally independently substituted by one to three substituents selected from F and R$^{10}$; phenoxy, optionally independently substituted by one to three substituents selected from F and R$^{10}$; Het$^2$; Het$^2$-oxy; and Het$^3$;
R$^{1a}$ and R$^{1b}$ are independently H, (C$_1$-C$_6$)alkyl or (C$_3$-C$_6$)cycloalkyl, optionally substituted, valency permitting, by one to eight F or, taken together with the N atom to which they are attached, form a 3- to 8-membered monoheterocycloalkyl, said monoheterocycloalkyl being optionally substituted on a ring carbon atom by, valency permitting, one to eight F;
R$^2$, R$^3$, R$^4$ are independently H, F, Cl or —OCH$_3$;
R$^5$ is H, CN, F, Cl, Het$^3$, or R$^6$;
R$^6$ is a group selected from (C$_1$-C$_6$)alkyl and (C$_1$-C$_6$)alkyloxy, wherein each group is optionally substituted, valency permitting, by one to eight F;
R$^7$ and R$^8$ are independently H; (C$_1$-C$_8$)alkyl, optionally independently substituted by one to three R$^{11}$; (C$_3$-C$_8$)cycloalkyl, optionally substituted by, valency permitting, one to eight F and/or by one to three R$^{10}$, and further optionally fused to a phenyl ring; 'C-linked' Het$^2$; or C-linked Het$^3$;
R$^9$ is (C$_1$-C$_6$)alkyloxy; (C$_3$-C$_8$)cycloalkyl, optionally substituted, valency permitting, by one to eight F; Het$^2$; or phenyl, optionally independently substituted by one to three R$^6$;
R$^{10}$ is Cl, CN or R$^6$;
R$^{11}$ is F; (C$_1$-C$_6$)alkyloxy; (C$_3$-C$_8$)cycloalkyl, optionally substituted, valency permitting, by one to eight F; 'C-linked' Het$^2$; or phenyl, optionally independently substituted by one to three R$^6$;
Het$^1$ is a 6-, 9- or 10-membered heteroaryl containing one to three nitrogen atoms;
Het$^2$ is a 3- to 8-membered saturated monoheterocycloalkyl containing one or two ring members selected from —NR$^{12}$— and —O—, said monoheterocycloalkyl being optionally substituted on a ring carbon atom by one to three substituents independently selected from F, (C$_1$-C$_6$)alkyl, (C$_1$-C$_4$)alkyloxy(C$_0$-C$_4$)alkylene and (C$_3$-C$_8$)cycloalkyl;
Het$^3$ is a 5- or 6-membered heteroaryl containing one to three nitrogen atoms, said heteroaryl being optionally substituted by one to three substituents selected from F, Cl, CN and R$^6$; and
R$^{12}$ is H, (C$_1$-C$_6$)alkyl or (C$_3$-C$_8$)cycloalkyl, wherein (C$_1$-C$_6$)alkyl and (C$_3$-C$_8$)cycloalkyl are optionally substituted, valency permitting, by one to eight F; or, when Het$^2$ is 'N-linked', is absent.

Described below are a number of embodiments (E) of this first aspect of the invention, where for convenience E1 is identical thereto.

E1 A compound of formula (I) as defined above or a pharmaceutically acceptable salt thereof.
E2 A compound according to E1 wherein X is —OCH$_2$—.
E3 A compound according to either E1 wherein X is —CH$_2$O—.
E4 A compound according to any of E1 to E3 wherein Z is phenyl optionally independently substituted by one to three substituents selected from Y$^1$ and Y$^2$.
E5 A compound according to any of E1 to E4 wherein Z is phenyl optionally independently substituted by one or two substituents selected from Y$^1$ and Y$^2$.
E6 A compound according to E1 wherein Z is a 6-membered heteroaryl comprising one to three nitrogen atoms, said heteroaryl being optionally independently substituted by one to three substituents selected from Y$^1$ and Y$^2$.
E7 A compound according to any of E1 or E6 wherein Z is pyridyl optionally independently substituted by one to three substituents selected from Y$^1$ and Y$^2$.
E8 A compound according to any of E1, E6 or E7 wherein Z is pyridyl optionally independently substituted by one or two substituents selected from Y$^1$ and Y$^2$.
E9 A compound according to any of E1 or E6 to E8 wherein Z is pyridyl optionally independently substituted by one or two substituents selected from Y$^1$ and Y$^2$ and wherein said pyridyl is orientated as below:

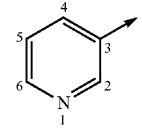

E10 A compound according to E9 wherein said pyridyl is 6-substituted or, where di-substituted, 5- and 6-substituted.
E11 A compound according to any of E1 to E10 wherein Y$^1$ and Y$^2$ are independently selected from F; Cl; CN; (C$_1$-C$_6$) alkyl, optionally substituted by, valency permitting, one to six F; (C$_1$-C$_8$)alkyloxy, optionally substituted by, valency permitting, one to eight F; (C$_3$-C$_6$)cycloalkyl, optionally substituted by, valency permitting, one to six F.
E12 A compound according to any of E1 to E11 wherein Y$^1$ and Y$^2$ are independently selected from F; Cl; CN; (C$_1$-C$_3$) alkyl, optionally substituted by one to three F; (C$_1$-C$_6$) alkyloxy, optionally substituted by, valency permitting, one to six F; (C$_3$-C$_4$)cycloalkyl, optionally substituted by one or two F.

E13 A compound according to any of E1 to E12 wherein $Y^1$ and $Y^2$ are independently selected from F; Cl; CN; $(C_1-C_2)$ alkyl, optionally substituted by one to three F; and $(C_1-C_4)$ alkyloxy.

E14 A compound according to any of E1 to E13 wherein $R^{1a}$ and $R^{1b}$ are independently $(C_1-C_3)$alkyl; $(C_3-C_5)$cycloalkyl; or, taken together with the N atom to which they are attached, form a 3- to 6-membered monoheterocycloalkyl, said monoheterocycloalkyl being optionally substituted on a ring carbon atom by one or two F.

E15 A compound according to any of E1 to E14 wherein $R^{1a}$ and $R^{1b}$ are independently $(C_1-C_3)$alkyl; or, taken together with the N atom to which they are attached, form a 3- to 6-membered monoheterocycloalkyl.

E16 A compound according to any of E1 to E15 wherein $R^{1a}$ and $R^{1b}$ are independently methyl.

E17 A compound according to any of E1 to E16 wherein $R^2$, $R^3$, $R^4$ and $R^5$ are independently H, F or Cl.

E18 A compound according to any of E1 to E17 wherein $R^2$, $R^3$, $R^4$ and $R^5$ are H.

E19 A compound according to any of E1 to E17 wherein $R^2$ and $R^5$ are independently selected from F or Cl, and $R^3$ and $R^4$ are both H.

E20 A compound according to any of E1 to E17, or E19, wherein $R^2$ is F, $R^3$ and $R^4$ are both H; and $R^5$ is F or Cl.

E21 A compound according to E1 selected from:
4-{[(5-Chloro-6-isopropoxypyridin-3-yl)oxy]methyl}-N-[(dimethylamino)sulfonyl]-2,5-difluorobenzamide;
4-{[3-Chloro-4-(trifluoromethyl)phenoxy]methyl}-N-[(dimethylamino)sulfonyl]-2,5-difluorobenzamide;
4-[(3,4-Dichlorobenzyl)oxy]-N-[(dimethylamino)sulfonyl]-2,5-difluorobenzamide;
4-{[4-chloro-3-(trifluoromethyl)phenoxy]methyl}-N-[(dimethylamino)sulfonyl]benzamide;
4-{[3-chloro-4-(trifluoromethyl)phenoxy]methyl}-N-[(dimethylamino)sulfonyl]benzamide;
4-{[4-chloro-3-(trifluoromethyl)phenoxy]methyl}-N-[(dimethylamino)sulfonyl]-2,5-difluorobenzamide;
4-[(5-chloro-6-isopropoxypyridin-3-yl)methoxy]-N-[(dimethylamino)sulfonyl]-2,5-difluorobenzamide;
4-[(4-chloro-3-fluorophenoxy)methyl]-N-[(dimethylamino)sulfonyl]-2,5-difluorobenzamide;
4-[(3-chloro-4-cyanophenoxy)methyl]-N-[(dimethylamino)sulfonyl]-2,5-difluorobenzamide;
4-[(3,4-dichlorophenoxy)methyl]-N-[(dimethylamino)sulfonyl]-2,5-difluorobenzamide;
4-[(3-chloro-4-fluorophenoxy)methyl]-N-[(dimethylamino)sulfonyl]-2,5-difluorobenzamide;
4-[(3,4-dichlorobenzyl)oxy]-N-[(dimethylamino)sulfonyl]benzamide;
N-(azetidin-1-ylsulfonyl)-4-{[(5-chloro-6-isopropoxypyridin-3-yl)oxy]methyl}-2,5-difluorobenzamide;
or a pharmaceutically acceptable salt thereof.

E22 A compound according to E1 selected from:
5-chloro-4-{[3-chloro-4-(trifluoromethyl)phenoxy]methyl}-N-[(dimethylamino)sulfonyl]-2-fluorobenzamide;
N-(azetidin-1-ylsulfonyl)-5-chloro-4-{[3-chloro-4-(trifluoromethyl)phenoxy]methyl}-2-fluorobenzamide;
N-(azetidin-1-ylsulfonyl)-4-{[3-chloro-4-(trifluoromethyl)phenoxy]methyl}-2,5-difluorobenzamide;
N-(azetidin-1-ylsulfonyl)-5-chloro-4-[(3,4-dichlorophenoxy)methyl]-2-fluorobenzamide;
N-(azetidin-1-ylsulfonyl)-4-[(3,4-dichlorophenoxy)methyl]-2,5-difluorobenzamide;
4-{[3-chloro-4-(trifluoromethoxy)phenoxy]methyl}-N-[(dimethylamino)sulfonyl]-2,5-difluorobenzamide;
5-chloro-4-({[5-chloro-6-(2,2,3,3,3-pentafluoropropoxy)pyridin-3-yl]oxy}methyl)-N-[(3,3-difluoroazetidin-1-yl)sulfonyl]-2-fluorobenzamide;
5-chloro-4-({[5-chloro-6-(2,2,3,3-tetrafluoropropoxy)pyridin-3-yl]oxy}methyl)-N-[(3,3-difluoroazetidin-1-yl)sulfonyl]-2-fluorobenzamide;
4-({[5-chloro-6-(2,2,2-trifluoro-1,1-dimethylethoxy)pyridin-3-yl]oxy}methyl)-N-[(3,3-difluoroazetidin-1-yl)sulfonyl]-2,5-difluorobenzamide;
4-({[5-chloro-6-(2,2,3,3,3-pentafluoropropoxy)pyridin-3-yl]oxy}methyl)-N-[(3,3-difluoroazetidin-1-yl)sulfonyl]-2,5-difluorobenzamide;
5-chloro-4-({[5-chloro-6-(2,2,3,3-tetrafluoropropoxy)pyridin-3-yl]oxy}methyl)-N-[(dimethylamino)sulfonyl]-2-fluorobenzamide;
N-(azetidin-1-ylsulfonyl)-5-chloro-4-({[5-chloro-6-(2,2,3,3-tetrafluoropropoxy)pyridin-3-yl]oxy}methyl)-2-fluorobenzamide;
5-chloro-4-({[5-chloro-6-(2,2,2-trifluoro-1,1-dimethylethoxy)pyridin-3-yl]oxy}methyl)-N-[(3,3-difluoroazetidin-1-yl)sulfonyl]-2-fluorobenzamide;
N-(azetidin-1-ylsulfonyl)-4-({[5-chloro-6-(2,2,3,3,3-pentafluoropropoxy)pyridin-3-yl]oxy}methyl)-2,5-difluorobenzamide;
4-({[5-chloro-6-(2,2,3,3,3-pentafluoropropoxy)pyridin-3-yl]oxy}methyl)-N-[(dimethylamino)sulfonyl]-2,5-difluorobenzamide;
N-(azetidin-1-ylsulfonyl)-5-chloro-4-({[5-chloro-6-(2,2,3,3,3-pentafluoropropoxy)pyridin-3-yl]oxy}methyl)-2-fluorobenzamide;
5-chloro-4-({[5-chloro-6-(2,2,3,3,3-pentafluoropropoxy)pyridin-3-yl]oxy}methyl)-N-[(dimethylamino)sulfonyl]-2-fluorobenzamide;
N-(azetidin-1-ylsulfonyl)-4-({[5-chloro-6-(2,2,2-trifluoro-1,1-dimethylethoxy)pyridin-3-yl]oxy}methyl)-2,5-difluorobenzamide;
4-({[5-chloro-6-(2,2,2-trifluoro-1,1-dimethylethoxy)pyridin-3-yl]oxy}methyl)-N-[(dimethylamino)sulfonyl]-2,5-difluorobenzamide;
5-chloro-4-{[(5-chloro-6-cyclopropylpyridin-3-yl)oxy]methyl}-N-[(3,3-difluoroazetidin-1-yl)sulfonyl]-2-fluorobenzamide;
5-chloro-4-({[5-chloro-6-(2,2,2-trifluoroethoxy)pyridin-3-yl]oxy}methyl)-N-[(3,3-difluoroazetidin-1-yl)sulfonyl]-2-fluorobenzamide;
N-(azetidin-1-ylsulfonyl)-5-chloro-4-({[5-chloro-6-(2,2,2-trifluoro-1,1-dimethylethoxy)pyridin-3-yl]oxy}methyl)-2-fluorobenzamide;
N-(azetidin-1-ylsulfonyl)-5-chloro-4-{[(5-chloro-6-cyclopropylpyridin-3-yl)oxy]methyl}-2-fluorobenzamide;
5-chloro-4-({[5-chloro-6-(3,3,3-trifluoropropoxy)pyridin-3-yl]oxy}methyl)-N-[(3,3-difluoroazetidin-1-yl)sulfonyl]-2-fluorobenzamide;
5-chloro-4-({[5-chloro-6-(2,2,2-trifluoro-1-methylethoxy)pyridin-3-yl]oxy}methyl)-N-[(dimethylamino)sulfonyl]-2-fluorobenzamide;
4-({[5-chloro-6-(2,2,3,3-tetrafluoropropoxy)pyridin-3-yl]oxy}methyl)-N-[(3,3-difluoroazetidin-1-yl)sulfonyl]-2,5-difluorobenzamide;
N-(azetidin-1-ylsulfonyl)-5-chloro-4-({[5-chloro-6-(2,2,2-trifluoroethoxy)pyridin-3-yl]oxy}methyl)-2-fluorobenzamide;
5-chloro-4-({[5-chloro-6-(3,3,3-trifluoropropoxy)pyridin-3-yl]oxy}methyl)-N-[(dimethylamino)sulfonyl]-2-fluorobenzamide;

N-(azetidin-1-ylsulfonyl)-5-chloro-4-({[5-chloro-6-(2,2,2-trifluoro-1-methylethoxy)pyridin-3-yl]oxy}methyl)-2-fluorobenzamide;
5-chloro-4-({[5-chloro-6-(2,2,2-trifluoro-1-methylethoxy)pyridin-3-yl]oxy}methyl)-N-[(3,3-difluoroazetidin-1-yl)sulfonyl]-2-fluorobenzamide;
5-chloro-4-({[5-chloro-6-(2,2,2-trifluoro-1,1-dimethylethoxy)pyridin-3-yl]oxy}methyl)-N-[(dimethylamino)sulfonyl]-2-fluorobenzamide;
5-chloro-4-{[(5-chloro-6-cyclopropylpyridin-3-yl)oxy]methyl}-N-[(dimethylamino)sulfonyl]-2-fluorobenzamide;
N-(azetidin-1-ylsulfonyl)-5-chloro-4-({[5-chloro-6-(3,3,3-trifluoropropoxy)pyridin-3-yl]oxy}methyl)-2-fluorobenzamide;
4-({[5-chloro-6-(2,2,3,3-tetrafluoropropoxy)pyridin-3-yl]oxy}methyl)-N-[(dimethylamino)sulfonyl]-2,5-difluorobenzamide;
5-chloro-4-({[5-chloro-6-(2,2,2-trifluoroethoxy)pyridin-3-yl]oxy}methyl)-N-[(dimethylamino)sulfonyl]-2-fluorobenzamide;
N-(azetidin-1-ylsulfonyl)-4-({[5-chloro-6-(2,2,3,3-tetrafluoropropoxy)pyridin-3-yl]oxy}methyl)-2,5-difluorobenzamide;
4-{[3-chloro-4-(trifluoromethyl)phenoxy]methyl}-N-[(3,3-difluoroazetidin-1-yl)sulfonyl]-2,5-difluorobenzamide;
N-(azetidin-1-ylsulfonyl)-4-{[4-chloro-3-(trifluoromethoxy)phenoxy]methyl}-2,5-difluorobenzamide;
N-(azetidin-1-ylsulfonyl)-5-chloro-4-{[4-chloro-3-(trifluoromethoxy)phenoxy]methyl}-2-fluorobenzamide;
4-[(3,4-dichlorophenoxy)methyl]-N-[(3,3-difluoroazetidin-1-yl)sulfonyl]-2,5-difluorobenzamide;
5-chloro-4-{[3-chloro-4-(trifluoromethyl)phenoxy]methyl}-N-[(3,3-difluoroazetidin-1-yl)sulfonyl]-2-fluorobenzamide;
N-(azetidin-1-ylsulfonyl)-4-{[3-chloro-4-(trifluoromethoxy)phenoxy]methyl}-2,5-difluorobenzamide;
4-{[4-chloro-3-(trifluoromethoxy)phenoxy]methyl}-N-[(3,3-difluoroazetidin-1-yl)sulfonyl]-2,5-difluorobenzamide;
5-chloro-4-[(3,4-dichlorophenoxy)methyl]-N-[(3,3-difluoroazetidin-1-yl)sulfonyl]-2-fluorobenzamide;
5-chloro-4-{[4-chloro-3-(trifluoromethoxy)phenoxy]methyl}-N-[(3,3-difluoroazetidin-1-yl)sulfonyl]-2-fluorobenzamide;
5-chloro-4-[(3,4-dichlorophenoxy)methyl]-N-[(dimethylamino)sulfonyl]-2-fluorobenzamide;
4-{[4-chloro-3-(trifluoromethoxy)phenoxy]methyl}-N-[(dimethylamino)sulfonyl]-2,5-difluorobenzamide;
N-(azetidin-1-ylsulfonyl)-5-chloro-4-{[3-chloro-4-(trifluoromethoxy)phenoxy]methyl}-2-fluorobenzamide;
4-{[4-chloro-3-(trifluoromethyl)phenoxy]methyl}-N-[(3,3-difluoroazetidin-1-yl)sulfonyl]-2,5-difluorobenzamide;
4-{[3-chloro-4-(trifluoromethoxy)phenoxy]methyl}-N-[(3,3-difluoroazetidin-1-yl)sulfonyl]-2,5-difluorobenzamide;
5-chloro-4-{[4-chloro-3-(trifluoromethoxy)phenoxy]methyl}-N-[(dimethylamino)sulfonyl]-2-fluorobenzamide;
N-(azetidin-1-ylsulfonyl)-4-{[4-chloro-3-(trifluoromethyl)phenoxy]methyl}-2,5-difluorobenzamide;
N-(azetidin-1-ylsulfonyl)-5-chloro-4-{[4-chloro-3-(trifluoromethyl)phenoxy]methyl}-2-fluorobenzamide;
5-chloro-4-{[4-chloro-3-(trifluoromethyl)phenoxy]methyl}-N-[(dimethylamino)sulfonyl]-2-fluorobenzamide;
5-chloro-4-{[3-chloro-4-(trifluoromethoxy)phenoxy]methyl}-N-[(3,3-difluoroazetidin-1-yl)sulfonyl]-2-fluorobenzamide;
5-chloro-4-{[4-chloro-3-(trifluoromethyl)phenoxy]methyl}-N-[(3,3-difluoroazetidin-1-yl)sulfonyl]-2-fluorobenzamide;
5-chloro-4-{[3-chloro-4-(trifluoromethoxy)phenoxy]methyl}-N-[(dimethylamino)sulfonyl]-2-fluorobenzamide;
or a pharmaceutically acceptable salt thereof.

Alkyl, alkylene, and alkoxy groups, containing the requisite number of carbon atoms, can be unbranched or branched. Examples of alkyl include methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy. Examples of alkylene include methylene, 1,1-ethylene, 1,2-ethylene, 1,1-propylene, 1,2-propylene, 1,3-propylene and 2,2-propylene.

Examples of cycloalkyl include cyclopropyl, cyclobutyl, cyclopentyl, cyclohexyl, cycloheptyl and cyclooctyl.

Halo means fluoro, chloro, bromo or iodo.

The term 'C-linked' used in the definitions of formula (I) means that the group in question is joined via a ring carbon. The term 'N-linked' used in the definitions of formula (I) means that the group in question is joined via a ring nitrogen.

Specific examples of 5- or 6-membered heteroaryl used in the definitions of formula (I) include pyrrolyl, pyrazolyl, imidazoyl, pyridyl, pyridazinyl, pyrimidinyl and pyrazinyl. Except as expressly defined above, when such heteroaryls are substituted, the substituent may be located on a ring carbon (in all cases) or a ring nitrogen with appropriate valency (if the substituent is joined through a carbon atom).

Specific examples of 9- or 10-membered heteroaryl used in the definitions of formula (I) include indolyl, benzimidazolyl, indazolyl, benzotriazolyl, pyrrolo[2,3-b]pyridyl, pyrrolo[2,3-c]pyridyl, pyrrolo[3,2-c]pyridyl, pyrrolo[3,2-b]pyridyl, imidazo[4,5-b]pyridyl, imidazo[4,5-c]pyridyl, pyrazolo[4,3-d]pyridyl, pyrazolo[4,3-c]pyridyl, pyrazolo[3,4-c]pyridyl, pyrazolo[3,4-b]pyridyl, isoindolyl, indazolyl, purinyl, indolizinyl, imidazo[1,2-a]pyridyl, imidazo[1,5-a]pyridyl, pyrazolo[1,5-a]pyridyl, pyrrolo[1,2-b]pyridazinyl, imidazo[1,2-c]pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-d]pyrazinyl and pyrido[3,4-b]pyrazinyl. Except as expressly defined above, when such heteroaryls are substituted, the substituent may be located on a ring carbon (in all cases) or a ring nitrogen with appropriate valency (if the substituent is joined through a carbon atom).

Specific examples of $Het^2$ include oxiranyl, aziridinyl, oxetanyl, azetidinyl, tetrahydrofuranyl, pyrrolidinyl, tetrahydropyranyl, piperidinyl, morpholinyl, piperazinyl, azepanyl, oxepanyl, oxazepanyl and diazepinyl.

Hereinafter, all references to compounds of the invention include compounds of formula (I) or pharmaceutically acceptable salts, solvates, or multi-component complexes thereof, or pharmaceutically acceptable solvates or multi-component complexes of pharmaceutically acceptable salts of compounds of formula (I), as discussed in more detail below.

Preferred compounds of the invention are compounds of formula (I) or pharmaceutically acceptable salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

The skilled person will appreciate that the aforementioned salts include ones wherein the counterion is optically active, for example d-lactate or l-lysine, or racemic, for example dl-tartrate or dl-arginine.

For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) may be prepared by one or more of three methods:
(i) by reacting the compound of formula (I) with the desired acid or base;
(ii) by removing an acid- or base-labile protecting group from a suitable precursor of the compound of formula (I) using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of formula (I) or pharmaceutically acceptable salts thereof may exist in both unsolvated and solvated forms. The term 'solvate' is used herein to describe a molecular complex comprising a compound of formula (I) or a pharmaceutically acceptable salt thereof and one or more pharmaceutically acceptable solvent molecules, for example, ethanol. The term 'hydrate' is employed when said solvent is water. Pharmaceutically acceptable solvates in accordance with the invention include those wherein the solvent of crystallization may be isotopically substituted, e.g. $D_2O$, $d_6$-acetone and $d_6$-DMSO.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995), incorporated herein by reference. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

Also included within the scope of the invention are multi-component complexes (other than salts and solvates) of compounds of formula (I) or pharmaceutically acceptable salts thereof wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004), incorporated herein by reference. For a general review of multi-component complexes, see J Pharm Sci, 64 (8), 1269-1288, by Haleblian (August 1975), incorporated herein by reference.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as $-COO^-Na^+$, $-COO^-K^+$, or $-SO_3^-Na^+$) or non-ionic (such as $-N^-N^+(CH_3)_3$) polar head group. For more information, see *Crystals and the Polarizing Microscope* by N. H. Hartshorne and A. Stuart, $4^{th}$ Edition (Edward Arnold, 1970), incorporated herein by reference.

The compounds of the invention may be administered as prodrugs. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs can, for example, be produced by replacing appropriate functionalities present in a compound of formula (I) with certain moieties known to those skilled in the art as 'pro-moieties' as described, for example, in "Design of Pro-drugs" by H Bundgaard (Elsevier, 1985).

Examples of prodrugs include phosphate prodrugs, such as dihydrogen or dialkyl (e.g. di-tert-butyl) phosphate prodrugs. Further examples of replacement groups in accordance with the foregoing examples and examples of other prodrug types may be found in the aforementioned references.

Also included within the scope of the invention are metabolites of compounds of formula (I), that is, compounds formed in vivo upon administration of the drug. Some examples of metabolites in accordance with the invention include, where the compound of formula (I) contains a phenyl (Ph) moiety, a phenol derivative thereof (-Ph>-PhOH);

Compounds of the invention containing one or more asymmetric carbon atoms can exist as two or more stereoisomers. Included within the scope of the invention are all stereoisomers of the compounds of the invention and mixtures of one or more thereof.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Mixtures of stereoisomers may be separated by conventional techniques known to those skilled in the art; see, for example, "Stereochemistry of Organic Compounds" by E. L. Eliel and S. H. Wilen (Wiley, New York, 1994.

The scope of the invention includes all crystal forms of the compounds of the invention, including racemates and racemic mixtures (conglomerates) thereof. Stereoisomeric conglomerates may also be separated by the conventional techniques described herein just above.

The scope of the invention includes all pharmaceutically acceptable isotopically-labelled compounds of the invention wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of the invention, for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection. Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Also within the scope of the invention are intermediate compounds as hereinafter defined, all salts, solvates and complexes thereof and all solvates and complexes of salts thereof as defined hereinbefore for compounds of formula (I). The invention includes all polymorphs of the aforementioned species and crystal habits thereof.

When preparing a compound of formula (I) in accordance with the invention, a person skilled in the art may routinely select the form of intermediate which provides the best combination of features for this purpose. Such features include the melting point, solubility, processability and yield of the intermediate form and the resulting ease with which the product may be purified on isolation.

The compounds of the invention may be prepared by any method known in the art for the preparation of compounds of analogous structure. In particular, the compounds of the invention can be prepared by the procedures described by reference to the Schemes that follow, or by the specific methods described in the Examples, or by similar processes to either.

The skilled person will appreciate that the experimental conditions set forth in the schemes that follow are illustrative of suitable conditions for effecting the transformations shown, and that it may be necessary or desirable to vary the precise conditions employed for the preparation of compounds of formula (I). It will be further appreciated that it may be necessary or desirable to carry out the transformations in a different order from that described in the schemes, or to modify one or more of the transformations, to provide the desired compound of the invention.

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino or carboxylic acid groups. The protecting groups used in the preparation of the compounds of the invention may be used in conventional manner. See, for example, those described in 'Greene's Protective Groups in Organic Synthesis' by Theodora W Greene and Peter G M Wuts, third edition, (John Wiley and Sons, 1999), in particular chapters 7 ("Protection for the Amino Group") and 5 ("Protection for the Carboxyl Group"), incorporated herein by reference, which also describes methods for the removal of such groups.

In the following general methods, $R^{1a}$, $R^{1b}$, $R^2$, $R^3$, $R^4$, $R^5$ and Z are as previously defined for a derivative of the formula (I) unless otherwise stated. Pg is a suitable carboxylic acid protecting group such as tert butyl, methyl, ethyl, or tolyl. W is —$CO_2Pg$ or CN. Lg is a suitable leaving group, such as halo (e.g. Br) or a sulphonate ester (e.g mesylate, triflate or tosylate). M is an optionally substituted/ligated metal or boron group suitable for cross coupling reactions, such as trialkylstannane, dihydroxyborane, dialkoxyborane or halozinc.

Where ratios of solvents are given, the ratios are by volume.

According to a first process, compounds of formula (I) wherein X is —$OCH_2$— may be prepared by the process illustrated in Scheme 1.

Compounds of formula (II) can be prepared by halogenation of the methyl group in compounds of formula (III) according to step (ii) using halogenating reagents. Conveniently, halogenation is effected using a reagent such as N-bromosuccinimide or N-iodosuccinimide (in the presence of radical initiators such as benzoyl peroxide or azobisisobutyronitrile), bromine, iodine, sodium bromate in a variety of solvents such as carbon tetrachloride, chloroform, dichloromethane, 1,2-dichloroethane, ethyl acetate, acetic acid and water. Preferred conditions are N-bromosuccinimide with azobisisobutyronitrile in 1,2-dichloroethane at reflux under illumination from a 100 Watt light-bulb.

Compounds of formula (III) can be made from compounds of formula (IV) according to reaction step (i) by activation of the acid group with reagents such as oxalyl chloride, carbonyl di-imidazole (CDI), a uronium based peptide coupling agent, propylphosphonic anhydride or a carbodiimide reagent followed by displacement with a sulfamide of formula (VI) in the presence of a nucleophilic base, such as 4-dimethylaminopyridine. Preferred conditions comprise N,N-dimethylaminopropyl-N'-ethylcarbodiimide and 4-dimethylaminopyridine in dichloromethane with N,N-dimethylsulfamide.

According to a second process, compounds of formula (I) wherein X is —$OCH_2$— may be prepared by the process illustrated in Scheme 2.

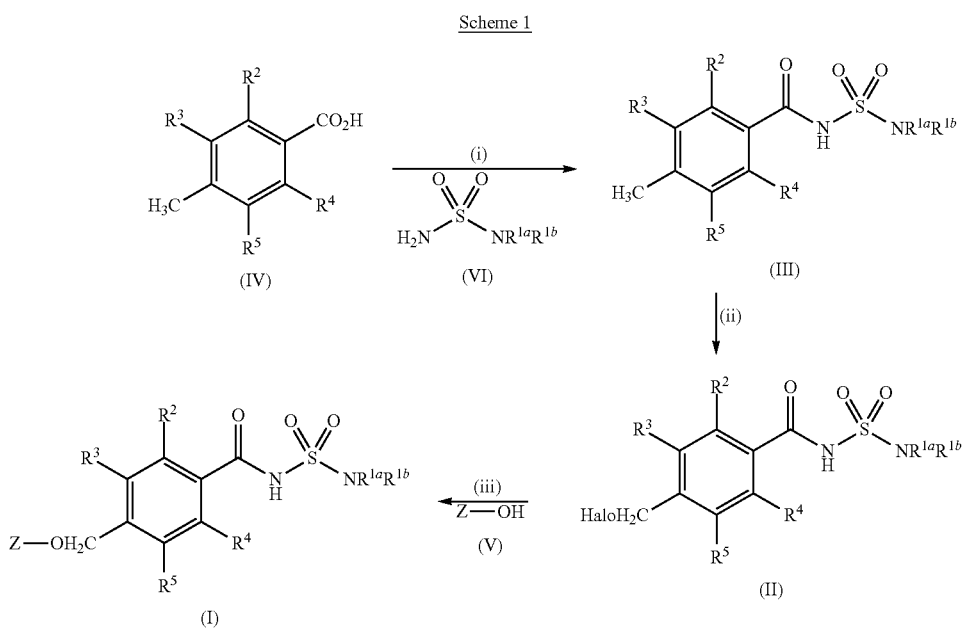

Scheme 1

(IV) → (i) → (III) → (ii) → (II) → (iii) Z—OH (V) → (I)

Compounds of formula (I) can be prepared from compounds of formula (II) (wherein halo is Br or I) according to step (iii) by nucleophilic displacement of halo by an alcohol of formula (V). Conveniently, the reaction is carried out in the presence of an auxiliary base such as triethylamine, N-ethyl-di-isopropylamine, potassium or sodium carbonate, sodium or potassium hydroxide in a variety of solvents such as NMP, dioxane, DMSO, acetone or DMF from room temperature to 150° C. Preferred conditions are potassium carbonate in DMSO at room temperature.

Compounds of formula (I) can be prepared from compounds of formulae (X) and (VI) according to reaction step (iv) under conditions described above in Scheme 1 step (i). Preferred conditions comprise N,N-dimethylaminopropyl-N'-ethylcarbodiimide and 4-dimethylaminopyridine in dichloromethane with N,N-dimethylsulfamide.

Compounds of formula (X) can be prepared from compounds of formula (IX, W=—$CO_2Pg$) according to step (iii) by hydrolysis of the ester functional group under acidic or basic conditions. Suitable acidic conditions include trifluoroacetic acid or HCl gas in a solvent such as dioxane or dichloromethane. Suitable basic conditions include lithium, sodium or potassium hydroxides in solvents such as THF, methanol or 1,4-dioxane. Preferred conditions are potassium hydroxide in ethanol/water at reflux or sodium hydroxide in methanol/water/THF at from room temperature to reflux.

imide with azobisisobutyronitrile in 1,2-dichloroethane at reflux under illumination from a 100 Watt light-bulb.

Compounds of formula (I) (X=CH$_2$O) can also be prepared from compounds of formula (III) by the process illustrated in Scheme 3.

Scheme 2

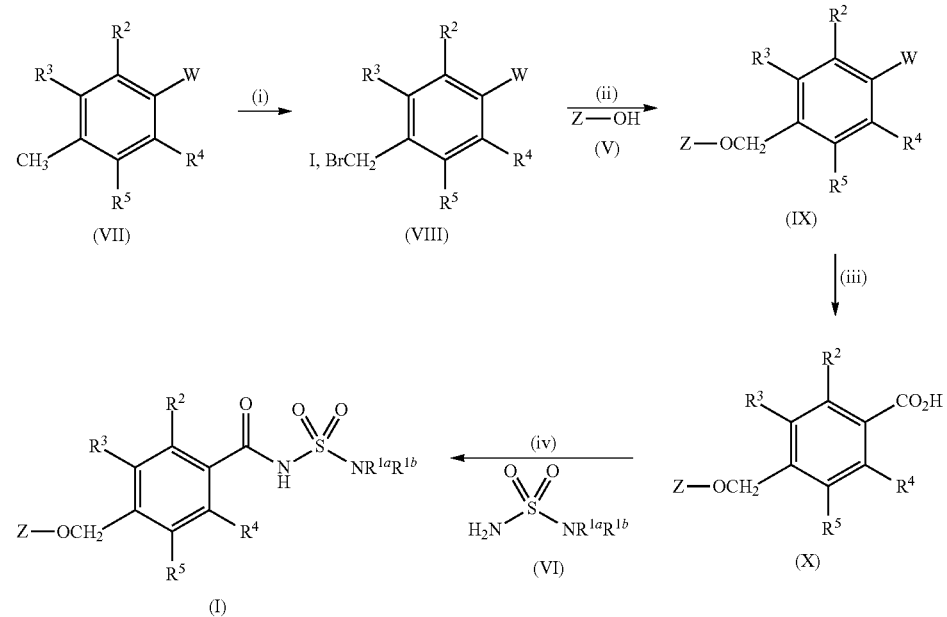

Alternatively, compounds of formula (X) can be prepared from compounds of formula (IX, W=CN) according to step (iii) by hydrolysis of the nitrile functional group under acidic or basic conditions. Suitable conditions are described just above. Preferred conditions are potassium hydroxide in ethanol/water at reflux.

Compounds of formula (IX) can be prepared from compounds of formula (VIII) according to step (ii) by nucleophilic displacement of the halogen group by an alcohol of formula (V) under conditions described above in Scheme 1 Step (iii). Preferred conditions are potassium carbonate in DMSO at room temperature.

Compounds of formula (VIII) can be prepared by halogenation of the methyl group in compounds of formula (VII) according to step (i) under conditions described above in Scheme 1 Step (ii). Preferred conditions are N-bromosuccin- Compounds of formula (I) can be prepared from compounds of formula (XIV) according to reaction step (iii) under conditions described above in Scheme 1 Step (i). Typical conditions comprise N,N-dimethylaminopropyl-N'-ethylcarbodiimide and 4-dimethylaminopyridine in dichloromethane.

Compounds of formula (XIV) can be prepared by hydrolysis of the ester functional group in compounds of formula (XIII) by either acidic or basic methods according to step (ii). Preferred conditions are lithium hydroxide in THF/water at 60° C.

According to a third process, compounds of formula (I) wherein X is —CH$_2$O— may be prepared by the process illustrated in Scheme 3.

Scheme 3

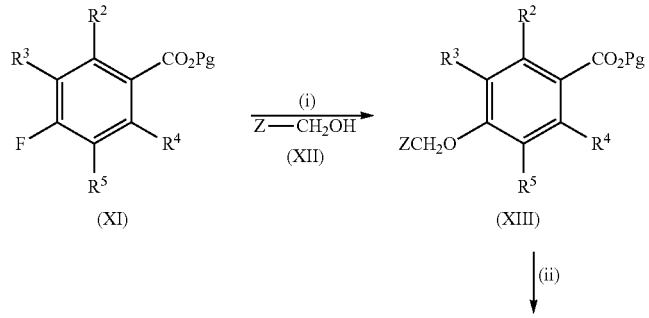

-continued

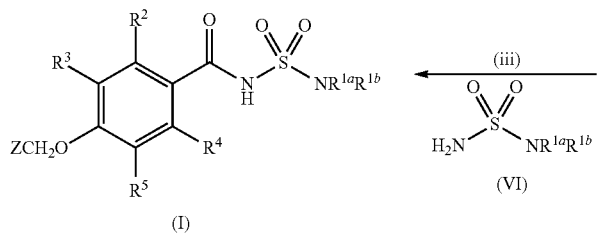 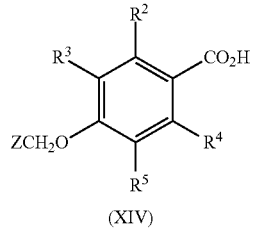

Compounds of formula (I) can be prepared according to process step (iii) by activation of the acid group of the compounds of formula (XIV), followed by displacement with a sulfamide of formula (VI) as described in Scheme 1 step (i).

Compounds of formula (XIV) can be prepared according to process step (ii) by hydrolysis of the carboxylic acid esters of formula (XIII), as described in Scheme 2 step (iii).

Compounds of formula (XIII) can be made from compounds of formula (XI) by a nucleophilic aromatic substitution reaction (SNAr) using an alcohol of formula (XII) and base, according to step (i). Suitable conditions include, potassium carbonate in DMF or DMSO, sodium hydride in NMP or DMF, sodium hydroxide or potassium hydroxide in 1,4-dioxane and water or DMSO or potassium tert-butoxide in THF, between room temperature and 150° C. Preferred conditions comprise 1 equivalent of potassium tert-butoxide in THF/DMSO at 80° C. for 16 hours.

According to a fourth process, compounds of formula (I) wherein X is —CH$_2$O— may be prepared by the process illustrated in Scheme 4.

Typical conditions comprise N,N-dimethylaminopropyl-N'-ethylcarbodiimide and 4-dimethylaminopyridine in dichloromethane.

Compounds of formula (XIII) can be prepared by hydrolysis of the ester functional group in compounds of formula (XVII) under conditions described in Scheme 3 step (ii). Preferred conditions are lithium hydroxide in tetrahydrofuran/water at 60° C.

Compounds of formula (XVII) can be made from compounds of formula (XV) according to process step (i) by a nucleophilic displacement (SN$_2$) reaction with compounds of formula (XVI) in the presence of a base. Suitable conditions include potassium carbonate in DMF or DMSO, sodium hydride in NMP or DMF, sodium hydroxide or potassium hydroxide in 1,4-dioxane and water or DMSO or potassium tert-butoxide in tetrahydrofuran between room temperature and 150° C. Preferred conditions comprise sodium hydride in tetrahydrofuran at room temperature for 48 hours.

Scheme 4

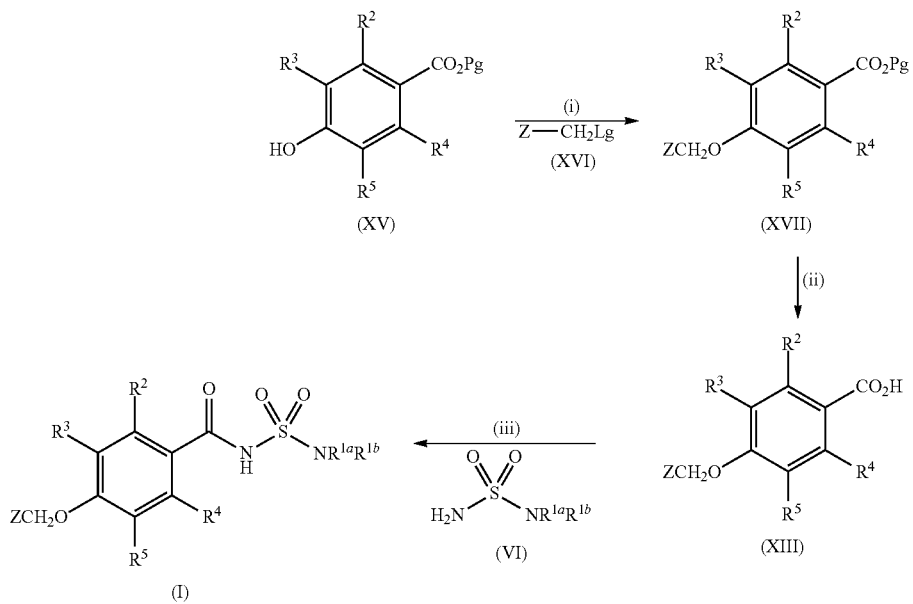

Compounds of formula (I) can be prepared from compounds of formulae (XIII) and (VI) according to reaction step (iii) under conditions described above in Scheme 1 step (i).

According to a fifth process, compounds of formula (I) wherein X is —CH$_2$O— may be prepared by the process illustrated in Scheme 5.

Scheme 5

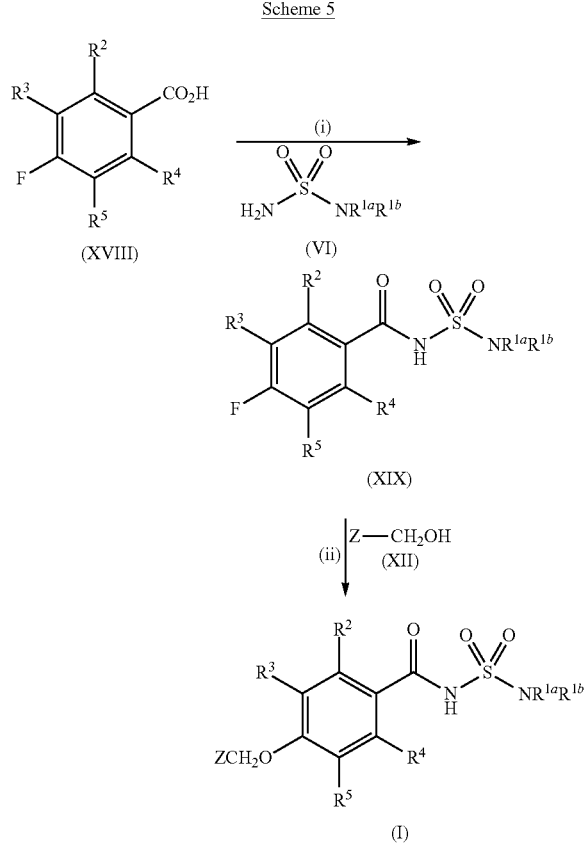

Compounds of formula (I) can be prepared from compounds of formula (XIX) according to process step (ii) by a nucleophilic aromatic substitution (SnAr) under conditions described above in Scheme 3 step (i). Preferred conditions comprise pre-forming the alkoxide in THF with sodium hydride at 55° C. followed by stirring with aryl fluorides of formulae (XIX) in DMSO from room to elevated temperatures of 120° C.

Compounds of formula (XIX) can be made from compounds of formula (XVIII) according to process step (i) under conditions described above in Scheme 1 step (i). Preferred conditions comprise potassium carbonate in DMSO at room temperature.

According to a sixth process, compounds of formula (I) wherein:
Z is

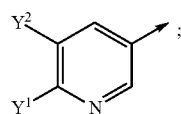

$Y^1$ is selected from $(C_1-C_8)$alkyloxy, optionally independently substituted by one to three $R^9$, and/or, valency permitting, by one to eight F; $(C_3-C_8)$cycloalkyloxy, optionally independently substituted, valency permitting, by one to eight F and/or by one to three $R^{10}$, and further optionally fused to a phenyl ring; phenoxy, optionally independently substituted, by one to three $R^{10}$; and $Het^2$-oxy; and
X is —CH$_2$O—;
may be prepared by the process illustrated in Scheme 6.

Compounds of formula (I) can be prepared from compounds of formulae (XXIII) and (VI) according to reaction step (iii) under conditions described above in Scheme 1 Step (i). Typical conditions comprise N,N-dimethylaminopropyl-N'-ethylcarbodiimide and 4-dimethylaminopyridine in dichloromethane.

Compounds of formula (XXIII) can be prepared from compounds of formula (XX) according to process step (vi) by a nucleophilic aromatic substitution reaction (SnAr) with alcohols of formula (XXII). Typical conditions comprise sodium hydride in THF at elevated temperatures, preferably 90° C.

Scheme 6

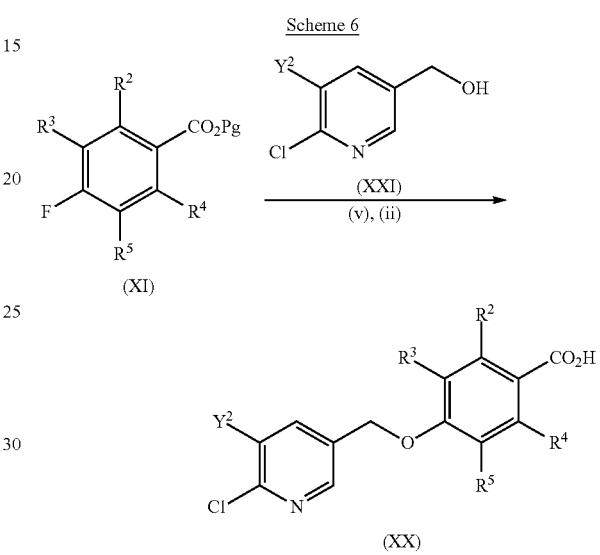

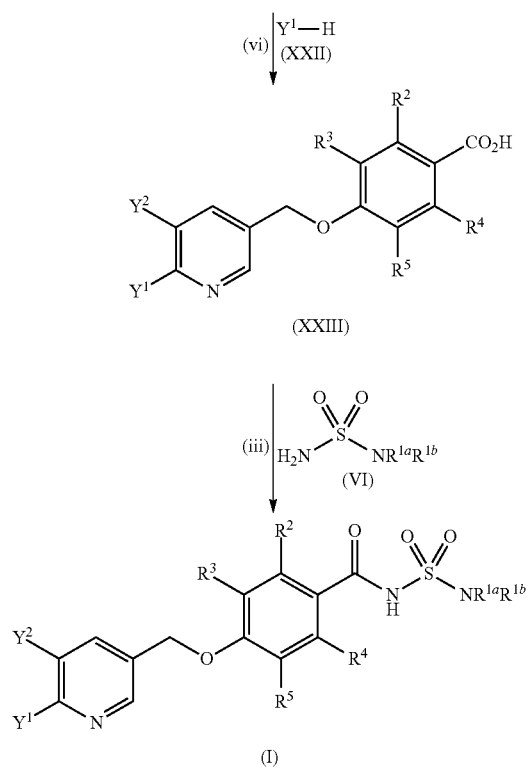

Compounds of formula (XX) can be prepared from compounds of formula (XI) according to process step (v) by a nucleophilic aromatic substitution reaction (SnAr) under conditions described above in Scheme 3 step (i), followed by hydrolysis of the ester functionality by either acidic or basic methods as described above, according to process step (ii). Preferred conditions comprise potassium carbonate in DMSO at room temperature followed by trifluoroacetic acid in dichloromethane at room temperature.

Compounds of formulae (IV), (V), (VI), (VII) (XI), (XII), (XV), (XVI), (XVIII), (XXI) and (XXII) are either commercially available, known from the literature, easily prepared by methods well known to those skilled in the art, or can be made according to preparations described herein.

All new processes for preparing compounds of formula (I), and corresponding new intermediates employed in such processes, form further aspects of the present invention.

Compounds of the invention intended for pharmaceutical use may be administered as crystalline or amorphous products or may exist in a continuum of solid states ranging from fully amorphous to fully crystalline. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

In another aspect the invention provides a pharmaceutical composition comprising a compound of the invention together with one or more pharmaceutically acceptable excipients.

Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

Suitable modes of administration include oral, parenteral, topical, inhaled/intranasal, rectal/intravaginal, and ocular/aural administration.

Formulations suitable for the aforementioned modes of administration may be formulated to be immediate and/or modified release. Modified release formulations include delayed-, sustained-, pulsed-, controlled-, targeted and programmed release.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films, ovules, sprays, liquid formulations and buccal/mucoadhesive patches.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet. Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant. Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. The formulation of tablets is discussed in "Pharmaceutical Dosage Forms: Tablets", Vol. 1, by H. Lieberman and L. Lachman (Marcel Dekker, New York, 1980).

Suitable modified release formulations for the purposes of the invention are described in U.S. Pat. No. 6,106,864. Details of other suitable release technologies such as high energy dispersions and osmotic and coated particles are to be found in "Pharmaceutical Technology On-line", 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents. Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™ Bioject™, etc.) injection.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

In the case of dry powder inhalers and aerosols, the dosage unit is determined by means of a valve which delivers a metered amount. Units in accordance with the invention are typically arranged to administer a metered dose or "puff" containing from 1 µg to 100 mg of the compound of formula (I). The overall daily dose will typically be in the range 1 µg to 200 mg which may be administered in a single dose or, more usually, as divided doses throughout the day.

The compounds of the invention may be administered rectally or vaginally, for example, in the form of a suppository, pessary, microbicide, vaginal ring or enema. Cocoa butter is a traditional suppository base, but various alternatives may be used as appropriate.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

For administration to human patients, the total daily dose of the compounds of the invention is typically in the range 1 mg to 10 g, such as 10 mg to 1 g, for example 25 mg to 500 mg depending, of course, on the mode of administration and efficacy. For example, oral administration may require a total daily dose of from 50 mg to 100 mg. The total daily dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

As noted above, the compounds of the invention are useful because they exhibit pharmacological activity in animals, i.e., Nav1.7 channel inhibition. More particularly, the compounds of the invention are of use in the treatment of disorders for which a Nav1.7 inhibitor is indicated. Preferably the animal is a mammal, more preferably a human.

In a further aspect of the invention there is provided a compound of the invention for use as a medicament.

In a further aspect of the invention there is provided a compound of the invention for the treatment of a disorder for which a Nav1.7 inhibitor is indicated.

In a further aspect of the invention there is provided use of a compound of the invention for the preparation of a medicament for the treatment of a disorder for which a Nav1.7 inhibitor is indicated.

In a further aspect of the invention there is provided a method of treating a disorder in an animal (preferably a mammal, more preferably a human) for which a Nav1.7 inhibitor is indicated, comprising administering to said animal a therapeutically effective amount of a compound of the invention.

Disorders for which a Nav1.7 inhibitor is indicated include pain, particularly neuropathic, nociceptive and inflammatory pain.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a heightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:
pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;
heart and vascular pain, including pain caused by angina, myocardical infarction, mitral stenosis, pericarditis, Raynaud's phenomenon, scleredoma and skeletal muscle ischemia;
head pain, such as migraine (including migraine with aura and migraine without aura), cluster headache, tension-type headache mixed headache and headache associated with vascular disorders;
erythermalgia; and
orofacial pain, including dental pain, otic pain, burning mouth syndrome and temporomandibular myofascial pain.

A Nav1.7 inhibitor may be usefully combined with another pharmacologically active compound, or with two or more other pharmacologically active compounds, particularly in the treatment of pain. Such combinations offer the possibility of significant advantages, including patient compliance, ease of dosing and synergistic activity.

In the combinations that follow the compound of the invention may be administered simultaneously, sequentially or separately in combination with the other therapeutic agent or agents.

A Nav1.7 inhibitor of formula (I), or a pharmaceutically acceptable salt thereof, as defined above, may be administered in combination with one or more agents selected from:
an alternative Nav1.7 channel modulator, such as another compound of the present invention or a compound disclosed in WO 2009/012242;
an alternative sodium channel modulator, such as a Nav1.3 modulator (e.g. as disclosed in WO2008/118758); or a Nav1.8 modulator (e.g. as disclosed in WO 2008/135826, more particularly N-[6-Amino-5-(2-chloro-5-methoxyphenyl)pyridin-2-yl]-1-methyl-1H-pyrazole-5-carboxamide);
an inhibitor of nerve growth factor signaling, such as: an agent that binds to NGF and inhibits NGF biological activity and/or downstream pathway(s) mediated by NGF signaling (e.g. tanezumab), a TrkA antagonist or a p75 antagoinsist;
a compound which increases the levels of endocannabinoid, such as a compound with fatty acid amid hydrolase inhibitory (FAAH) activity, in particular those disclosed in WO 2008/047229 (e.g. N-pyridazin-3-yl-4-(3-{[5-(trifluoromethyl)pyridine-2-yl]oxy}benzylidene) piperidene-1-carboxamide);
an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;
a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobartital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an $H_1$ antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl) quinazoline;

a tricyclic antidepressant, e.g. desipramine, imipramine, amitriptyline or nortriptyline;

an anticonvulsant, e.g. carbamazepine, lamotrigine, topiratmate or valproate;

a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

a vanilloid receptor agonist (e.g. resinferatoxin) or antagonist (e.g. capsazepine);

a beta-adrenergic such as propranolol;

a local anaesthetic such as mexiletine;

a corticosteroid such as dexamethasone;

a 5-HT receptor agonist or antagonist, particularly a $5-HT_{1B/1D}$ agonist such as eletriptan, sumatriptan, naratriptan, zolmitriptan or rizatriptan;

a $5-HT_{2A}$ receptor antagonist such as R(+)-alpha-(2,3-dimethoxy-phenyl)-1-[2-(4-fluorophenylethyl)]-4-piperidinemethanol (MDL-100907);

a $5-HT_3$ antagonist, such as ondansetron a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol®;

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-Nyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminoethyl-5-methyl-heptanoic acid, (3S,5R)-3-amino-5-methyl-thyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buprorion, buprorion metabolite hydroxybuprorion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl) amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S, 4R)-2-amino-4-[[2-chloro-5-(trifluoromethyl)phenyl] thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino) ethyl]phenyl]thiophene-2-carboxamidine, or guanidinoethyldisulfide;

an acetylcholinesterase inhibitor such as donepezil;

a prostaglandin $E_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methyl-benzenesulfonamide or 4-[(1S)-1-({[5-chloro-2-(3-fluorophenoxy)pyridin-3-yl]carbonyl}amino)ethyl] benzoic acid;

a microsomal prostaglandin E synthase type 1 (mPGES-1) inhibitor;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870;

a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl),1,4-benzoquinone (CV-6504).

There is also included within the scope the present invention combinations of a compound of the invention together with one or more additional therapeutic agents which slow down the rate of metabolism of the compound of the invention, thereby leading to increased exposure in patients. Increasing the exposure in such a manner is known as boosting. This has the benefit of increasing the efficacy of the compound of the invention or reducing the dose required to achieve the same efficacy as an unboosted dose. The metabolism of the compounds of the invention includes oxidative processes carried out by P450 (CYP450) enzymes, particularly CYP 3A4 and conjugation by UDP glucuronosyl transferase and sulphating enzymes. Thus, among the agents that may be used to increase the exposure of a patient to a compound of the present invention are those that can act as inhibitors of at least one isoform of the cytochrome P450 (CYP450) enzymes. The isoforms of CYP450 that may be beneficially inhibited include, but are not limited to, CYP1A2, CYP2D6, CYP2C9, CYP2C19 and CYP3A4. Suitable agents that may be used to inhibit CYP 3A4 include ritonavir, saquinavir, ketoconazole, N-(3,4-difluorobenzyl)-N-methyl-2-{[(4-methoxypyridin-3-yl)amino]sulfonyl}benzamide and N-(1-(2-(5-(4-fluorobenzyl)-3-(pyridin-4-yl)-1H-pyrazol-1-yl) acetyl)piperidin-4-yl)methanesulfonamide.

It is within the scope of the invention that two or more pharmaceutical compositions, at least one of which contains a compound of the invention, may conveniently be combined in the form of a kit suitable for coadministration of the compositions. Thus the kit of the invention comprises two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like. The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

In another aspect the invention provides a pharmaceutical product (such as in the form of a kit) comprising a compound of the invention together with one or more additional therapeutically active agents as a combined preparation for simultaneous, separate or sequential use in the treatment of a disorder for which a Nav1.7 inhibitor is indicated.

It is to be appreciated that all references herein to treatment include curative, palliative and prophylactic treatment.

In the non-limiting Examples and Preparations that are set out later in the description, and in the aforementioned Schemes, the following the abbreviations, definitions and analytical procedures may be referred to:

AcOH is acetic acid, $Cs_2CO_3$ is caesium carbonate;

$Cu(acac)_2$ is copper (II) acetylacetonate;

CuI is copper (I) iodide;

$Cu(OAc)_2$ is copper (II) acetate;

DAD is diode array detector;

DCM is dichloromethane; methylene chloride;

DIPEA is N-ethyldiisopropylamine, N,N-diisopropylethylamine;

DMAP is 4-dimethylaminopyridine;

DMF is N,N-dimethylformamide;

DMSO is dimethyl sulphoxide;

EDCI is 1-(3-dimethylaminopropyl)-3-ethylcarbodiimide hydrochloride;

EDTA is ethylenediaminetetraacetic acid;

ELSD is evaporative light scattering detection;

$Et_2O$ is diethyl ether;

EtOAc is ethyl acetate;

EtOH is ethanol;

HCl is hydrochloric acid;

IPA is isopropanol;

$Ir_2(OMe)_2COD_2$ is bis(1,5-cyclooctadiene)di-µ-methoxydiiridium (I);

$K_2CO_3$ is potassium carbonate;

$KHSO_4$ is potassium hydrogen sulphate;

KOAc is potassium acetate;

KOH is potassium hydroxide;

$K_3PO_4$ is potassium phosphate tribasic;

LCMS is liquid chromatography mass spectrometry ($R_t$=retention time)

LiOH is lithium hydroxide;

MeOH is methanol;

$MgSO_4$ is magnesium sulphate;

NaH is sodium hydride;

$NaHCO_3$ is sodium hydrogencarbonate;

$Na_2CO_3$ is sodium carbonate;

$NaHSO_3$ is sodium bisulphate;

$NaHSO_4$ is sodium hydrogensulphate;

NaOH is sodium hydroxide;

$Na_2SO_4$ is sodium sulphate;

NBS is N-bromosuccinimide;
NH$_4$Cl is ammonium chloride;
NMP is N-Methyl-2-pyrrolidone;
Pd/C is palladium on carbon;
Pd(PPh$_3$)$_4$ is tetrakis(triphenylphosphine)palladium(0);
Pd(dppf)$_2$Cl$_2$ is [1,1'-bis(diphenylphosphino)ferrocene]dichloropalladium(II), complex with dichloromethane;
THF is tetrahydrofuran;
THP is tetrahydropyran;
TLC is thin layer chromatography; and
WSCDI is 1-(3-dimethylaminopropyl)-3-ethylcarbodiimide hydrochloride.

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The following abbreviations have been used for common solvents: CDCl$_3$, deuterochloroform; d$_6$-DMSO, deuterodimethylsulphoxide; and CD$_3$OD, deuteromethanol.

Mass spectra, MS (m/z), were recorded using either electrospray ionisation (ESI) or atmospheric pressure chemical ionisation (APCI). When relevant, m/z data provided may include isotopes $^{35}$Cl, $^{37}$Cl, $^{79}$Br, $^{81}$Br and combinations there of.

Automated Preparative High Performance Liquid Chromatography (Auto-HPLC)

Certain compounds of the Examples and Preparations were purified using Automated Preparative High Performance Liquid Chromatography (HPLC). Reversed-phase HPLC conditions were either on Fraction Lynx systems or on a Trilution system.

In the case of the Fractionlynx system, Samples were submitted dissolved in 1 mL of DMSO. Depending on the nature of the compounds and the results of a pre-analysis, the purification was performed under either acidic ('A-HPLC'), or basic ('B-HPLC') conditions at ambient temperature. A-HPLC was carried out on a Sunfire Prep C18 OBD column (19×100 mm, 5 μm). B-HPLC was carried out on an Xterra Prep MS C18 (19×100 mm, 5 μm), both from Waters. A flow rate of 18 mL/min was used with mobile phase A: water+0.1% modifier (v/v) and B: acetonitrile+0.1% modifier (v/v). For acidic runs the modifier was formic acid, for basic run the modifier was diethylamine. A Waters 2525 binary LC pump supplied a mobile phase with a composition of 5% B for 1 min then ran from 5% to 98% B over 6 min followed by a 2 min hold at 98% B.

Detection was achieved using a Waters 2487 dual wavelength absorbance detector set at 225 nm followed in series by a Polymer Labs PL-ELS 2100 detector and a Waters ZQ 2000 4 way MUX mass spectrometer in parallel. The PL 2100 ELSD was set at 30° C. with 1.6 L/min supply of Nitrogen. The Waters ZQ MS was tuned with the following parameters:

| ES+ Cone voltage: 30 v | Capillary: 3.20 kv |
| ES– Cone voltage: –30 v | Capillary: –3.00 kv |

Desolvation gas: 600 L/hr
Source Temp: 120° C.
Scan range 150-900 Da
The fraction collection was triggered by both MS and ELSD.

Quality control (QC) analysis was performed using a LCMS method. Acidic runs were carried out on a Sunfire C18 (4.6×50 mm, 5 μm), basic runs were carried out on a Xterra C18 (4.6×50 mm, 5 μm), both from Waters. A flow rate of 1.5 mL/min was used with mobile phase A: water+0.1% modifier (v/v) and B: acetonitrile+0.1% modifier (v/v). For acidic runs the modifier was formic acid, for basic run the modifier was ammonia. A Waters 1525 binary LC pump ran a gradient elution from 5% to 95% B over 3 min followed by a 1 min hold at 95% B. Detection was achieved using a Waters MUX UV 2488 detector set at 225 nm followed in series by a Polymer Labs PL-ELS 2100 detector and a Waters ZQ 2000 4 way MUX mass spectrometer in parallel. The PL 2100 ELSD was set at 30° C. with 1.6 L/min supply of Nitrogen. The Waters ZQ MS was tuned with the following parameters:

| ES+ Cone voltage: 25 v | Capillary: 3.30 kv |
| ES– Cone voltage: –30 v | Capillary: –2.50 kv |

Desolvation gas: 800 L/hr
Source Temp: 150° C.
Scan range 160-900 Da

Where the reversed-phase Trilution system was used (T-HPLC) the conditions were as follows:
Mobile phase A: 0.1% formic acid in water
Mobile phase B: 0.1% formic acid in acetonitrile
Column: Phenomenex C18 Luna 21.5 mm×15 cm with 5 micron particle size
Gradient: 95-5% A over 15 min, 15 min hold, 15 ml/min flow rate
UV: 200 nm-400 nm
Temperature: Room temperature Liquid Chromatography Mass Spectrometry Unless carried out by Auto-HPLC (under conditions of A-HPLC or B-HPLC) as described just above, or as specifically set out in the Examples and Preparations that follow, LCMS conditions were run according to one of the conditions given below (where ratios of solvents are given, the ratios are by volume):

Acidic 2 Minute LCMS
Mobile phase A: 0.1% formic acid in water
Mobile phase B: 0.1% formic acid in 70% methanol:30% isopropanol
Column: C18 phase Phenomenex 20×4.0 mm with 3 micron particle size
Gradient: 98-10% A over 1.5 min, 0.3 min hold, 0.2 re-equilibration, 2 ml/min flow rate
UV: 210 nm-450 nm DAD
Temperature: 75° C.
Or
Mobile phase A: 0.1% formic acid in water
Mobile phase B: 0.1% formic acid in acetonitrile
Column: C18 phase Phenomenex 20×4.0 mm with 3 micron particle size
Gradient: 70-2% A over 1.5 min, 0.3 min hold, 0.2 re-equilibration, 1.8 ml/min flow rate
UV: 210 nm-450 nm DAD
Temperature: 75° C.

Acidic 4.5 Minute LCMS
Mobile phase A: 0.05% formic acid in water
Mobile phase B: acetonitrile
Column: Phenomenex Gemini C18 45×45 mm with 5 micron particle size
Gradient: 80-50% A over 0.5 min, 50-2% A over 3 min, 1 min hold, 0.2 min re-equilibration, 2.0 ml/min flow rate
UV: 220 nm-254 nm DAD
Temperature: 40° C.

Acidic 8 Minute LCMS
Mobile phase A: 0.05% formic acid in water
Mobile phase B: acetonitrile Column: Phenomenex Gemini C18 45×45 mm with 5 micron particle size
Gradient: 80-50% A over 0.5 min, 50-2% A over 3 min, 4.5 min hold, 0.2 min re-equilibration, 2.0 ml/min flow rate
UV: 220 nm-254 nm DAD
Temperature: 40° C.
Acidic 6 Minute LCMS
Mobile phase A: 0.1% formic acid in water
Mobile phase B: 0.1% formic acid in acetonitrile
Column: C18 phase Waters Sunfire 50×4.6 mm with 5 micron particle size
Gradient: 95-5% A over 3 min, 1 min hold, 2 min re-equilibration, 1.5 ml/min flow rate
UV: 210 nm-450 nm DAD
Temperature: 50° C.
Basic 6 minute LCMS
Mobile phase A: 0.1% ammonium hydroxide in water
Mobile phase B: 0.1% ammonium hydroxide in acetonitrile
Column: C18 phase Fortis 50×4.6 mm with 5 micron particle size
Gradient: 95-5% A over 3 min, 1 min hold, 2 min re-equilibration, 1 ml/min flow rate
UV: 210 nm-450 nm DAD
Temperature: 50° C.
Acidic 30 Minute LCMS
Mobile phase A: 0.1% formic acid in water
Mobile phase B: 0.1% formic acid in acetonitrile
Column: Phenomenex C18 phase Gemini 150×4.6 mm with 5 micron particle size
Gradient: 98-2% A over 18 min, 2 min hold, 1 ml/min flow rate
UV: 210 nm-450 nm DAD
Temperature: 50° C.
Basic 30 Minute LCMS
Mobile phase A: 10 mM ammonium acetate in water
Mobile phase B: 10 mM ammonium acetate in methanol
Column: Phenomenex Phenyl Hexyl 150×4.6 mm with 5 micron particle size
Gradient: 98-2% A over 18 min, 2 min hold, 1 ml/min flow rate
UV: 210 nm-450 nm DAD
Temperature: 50° C.

EXAMPLE 1

4-{[(5-Chloro-6-isopropoxypyridin-3-yl)oxy]methyl}-N-[(dimethylamino)sulfonyl]-2,5-difluorobenzamide

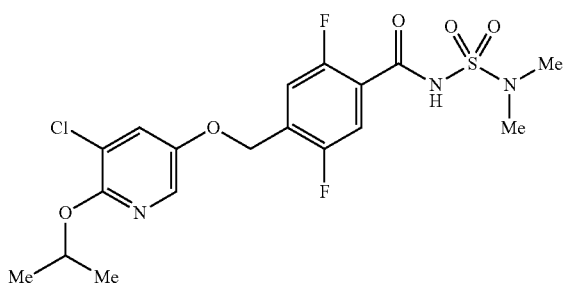 [SMILES: CC(C)Oc1ncc(OCc2cc(F)c(C(=O)NS(=O)(=O)N(C)C)cc2F)cc1Cl]

A solution of 5-chloro-6-isopropoxypyridin-3-ol (Preparation 6, 44 mg, 0.232 mmol), 4-(bromomethyl)-N-[(dimethylamino)sulfonyl]-2,5-difluorobenzamide (Preparation 1, 83 mg, 0.23 mmol) and potassium carbonate (64 mg, 0.47 mmol) in dimethyl sulfoxide (5 mL) was stirred at room temperature for 16 hours. The reaction mixture was diluted with water (20 mL) and acidified to ~pH 4 using acetic acid (2 mL). The resulting precipitate was filtered, washed with water (20 mL) and dried to afford the title compound as a white solid (32 mg).
$^1$H NMR (400 MHz, d$_6$-DMSO): δ 1.25 (d, 6H), 2.85 (s, 6H), 5.20 (m, 1H), 5.22 (s, 2H), 7.59 (m, 2H), 7.80 (m, 1H), 7.95 (m, 1H), 12.00 (bs, 1H).
LCMS Rt=3.63 minutes MS m/z 462 [M$^{35}$Cl—H]$^-$

EXAMPLE 2

4-{[3-Chloro-4-(trifluoromethyl)phenoxy]methyl}-N-[(dimethylamino)sulfonyl]-2,5-difluorobenzamide

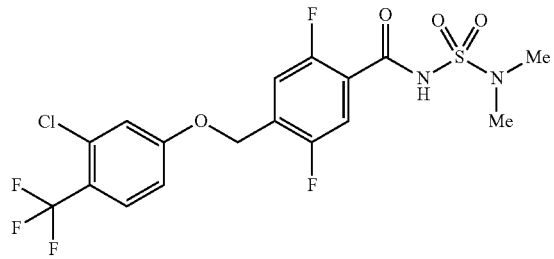 [SMILES: CN(C)S(=O)(=O)NC(=O)c1cc(F)c(COc2ccc(C(F)(F)F)c(Cl)c2)cc1F]

To a solution of 4-(bromomethyl)-N-[(dimethylamino)sulfonyl]-2,5-difluorobenzamide (Preparation 1, 167 mg, 0.47 mmol) in dimethylsulfoxide (2 mL) was added 2-chloro-4-hydroxybenzotrifluoride (92 mg, 0.47 mmol) followed by addition of potassium carbonate (129 mg, 0.94 mmol). The reaction was left to stir at room temperature for 18 hours. The reaction was diluted with dichloromethane (20 mL) and washed with aqueous potassium hydrogen sulfate (5 mL). The organic phase was separated and the aqueous phase extracted with dichloromethane (2×20 mL). The combined organic layers were washed with brine (30 mL) and filtered through a phase separation cartridge. The solvent was removed under reduced pressure and the crude product purified by reverse phase preparative HPLC. The correct fractions were combined and reduced to dryness to afford the title compound as white solid (23 mg, 10%).
$^1$H NMR (400 MHz, CDCl$_3$): δ 3.05 (s, 6H), 5.20 (s, 2H), 6.92 (m, 1H), 7.12 (d, 1H), 7.39 (m, 1H), 7.64 (d, 1H), 7.82 (dd, 1H), 8.75 (br s, 1H).
LCMS Rt=4.02 minutes MS m/z 471 [M$^{35}$Cl—H]$^-$

EXAMPLE 3

4-[(3,4-Dichlorobenzyl)oxy]-N-[(dimethylamino)sulfonyl]-2,5-difluorobenzamide

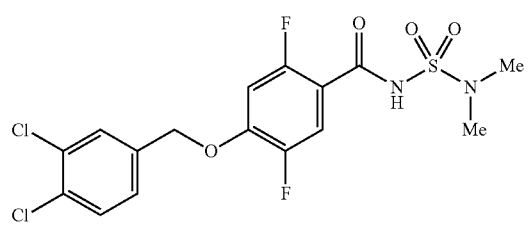 [SMILES: CN(C)S(=O)(=O)NC(=O)c1cc(F)c(OCc2ccc(Cl)c(Cl)c2)cc1F]

To a solution of 3,4-dichlorobenzyl alcohol (157 mg, 0.884 mmol) in tetrahydrofuran (3 mL) was added sodium hydride (60% dispersion in oil, 37 mg, 0.92 mmol). The reaction was stirred at room temperature for 45 minutes and heated to 55° C. for 30 minutes. The reaction mixture was cooled to room temperature and concentrated in vacuo. To the residue was added a solution of N-[(dimethylamino)sulfonyl]-2,4,5-trifluorobenzamide (Preparation 3, 100 mg, 0.354 mmol) in dimethyl sulfoxide (2 mL). The reaction mixture was stirred at room temperature for 3 hours and then partitioned between aqueous 2M hydrochloric acid (5 mL) and ethyl acetate (10 mL). The organic phase was separated and washed with a saturated aqueous solution of sodium chloride (10 mL), dried over magnesium sulfate, filtered and concentrated in vacuo. The crude material was triturated with diethyl ether, filtered and dried in vacuo to afford the title compound as a white solid (56 mg, 29%).

$^1$H NMR (400 MHz, CDCl$_3$): δ 3.05 (s, 6H), 5.15 (s, 2H), 6.72-6.82 (m, 1H), 7.25-7.30 (m, 1H), 7.47-7.57 (m, 2H), 7.78-7.88 (m, 1H), 8.60-8.73 (br s, 1H).

LCMS Rt=3.11 minutes MS m/z 437 [M$^{35}$Cl—H]$^-$

EXAMPLE 4

4-{[4-chloro-3-(trifluoromethyl)phenoxy]methyl}-N-[(dimethylamino)sulfonyl]benzamide

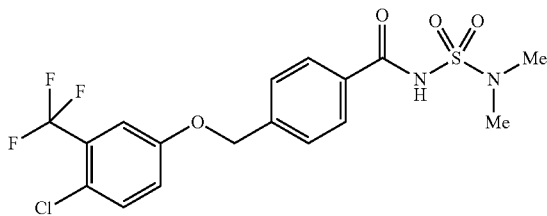 [SMILES: CN(C)S(=O)(=O)NC(=O)c1ccc(COc2ccc(Cl)c(C(F)(F)F)c2)cc1]

To a solution of 4-{[4-chloro-3-(trifluoromethyl)phenoxy]methyl}benzoic acid (Preparation 16, 237 mg, 0.72 mmol) in dichloromethane (8 mL) was added EDCI (344 mg, 1.79 mmol) followed by addition of N,N-dimethylsulfamide (222 mg, 1.79 Calculation isn't correct mmol). The reaction was left to stir at room temperature for 3 hours. A solution of KHSO4 (10 mL) was added and the mixture separated using a phase separation cartridge. The organics were dried in vacuo to yield a white solid as the title compound (285 mg, 97%).

$^1$NMR (400 MHz, CDCl$_3$): δ 2.95 (s, 6H), 5.10 (s, 2H), 7.00 (dd, 1H), 7.23 (d, 1H), 7.36 (d, 1H), 7.49 (d, 2H), 7.89 (d, 2H).

LCMS Rt=1.74 minutes MS m/z 406 [M$^{35}$Cl—H]$^-$

EXAMPLE 5

4-{[3-chloro-4-(trifluoromethyl)phenoxy]methyl}-N-[(dimethylamino)sulfonyl]benzamide

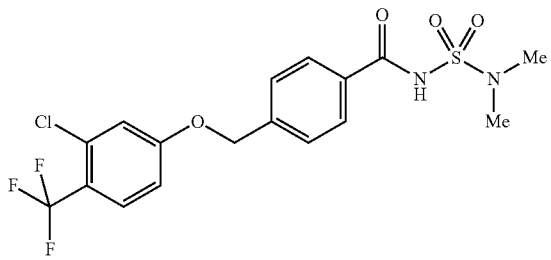 [SMILES: CN(C)S(=O)(=O)NC(=O)c1ccc(COc2ccc(C(F)(F)F)c(Cl)c2)cc1]

To a solution of ethyl 4-{[3-chloro-4-(trifluoromethyl)phenoxy]methyl}benzoate (Preparation 18, 125 mg, 0.35 mmol) in methanol (5.0 mL) was added water (2.0 mL) followed by sodium hydroxide (140 mg, 3.5 mmol). The reaction mixture was heated to 55° C. for 18 hours, then cooled and diluted with EtOAc (50 mL) and 2M HCl (50 mL). The aqueous layer was separated and washed with EtOAc (2×50 mL). The combined organics were dried over magnesium sulfate, filtered and concentrated in vacuo to yield 4-{[3-chloro-4-(trifluoromethyl)phenoxy]methyl}benzoic acid as an off-white solid (90 mg, 78% yield). This solid was dissolved in dichloromethane (3 mL) then EDCI (344 mg, 1.79 mmol) and DMAP (88 mg, 0.70 mmol) were added, followed by the addition of N,N-dimethylsulfamide (86 mg, 0.70 mmol). The reaction was left to stir at room temperature for 2 hours. A solution of 2M HCl (10 mL) was added and the mixture separated using a phase separation cartridge. The organics were dried in vacuo to yield a solid which was triturated with heptane:IPA (4:1, 100 mL) and sonicated. The supernatant was decanted and the residue dried in vacuo to yield an off-white solid as the title compound (57 mg, 38% yield).

$^1$H NMR (400 MHz, CDCl$_3$): δ 3.05 (s, 6H), 5.17 (s, 2H), 6.90 (m, 1H), 7.10 (d, 1H), 7.54 (d, 2H), 7.61 (d, 1H), 7.86 (d, 2H), 8.51 (br s, 1H).

LCMS Rt=1.56 minutes MS m/z 435 [M$^{35}$Cl—H]$^-$

EXAMPLE 6

4-{[4-chloro-3-(trifluoromethyl)phenoxy]methyl}-N-[(dimethylamino)sulfonyl]-2,5-difluorobenzamide

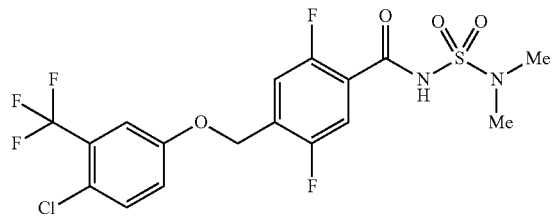 [SMILES: CN(C)S(=O)(=O)NC(=O)c1cc(F)c(COc2ccc(Cl)c(C(F)(F)F)c2)cc1F]

To a solution of 4-(bromomethyl)-N-[(dimethylamino)sulfonyl]-2,5-difluorobenzamide (Preparation 1, 146 mg, 0.409 mmol) in DMSO (5 mL) were added 4-chloro-3-(trifluoromethyl)phenol (80 mg, 0.409 mmol) and K$_2$CO$_3$ (113 mg, 0.818 mmol). The reaction was stirred at room temperature for 16 hours. KHSO$_4$ (5 mL) was added to the reaction mixture followed by water (30 mL) and DCM (20 mL). The organic was separated and the aqueous was re-extracted into DCM (2×20 mL). The combined organics were washed with brine (50 mL), filtered through a phase separation cartridge and reduced to dryness to give a white solid (197 mg). The residue was purified using reverse phase preparative HPLC to afford the title compound as the diethylamine salt.

LCMS Rt=3.66 minutes MS m/z 473 [M$^{35}$ClH]+

EXAMPLE 7

4-[(5-chloro-6-isopropoxypyridin-3-yl)methoxy]-N-[(dimethylamino)sulfonyl]-2,5-difluorobenzamide

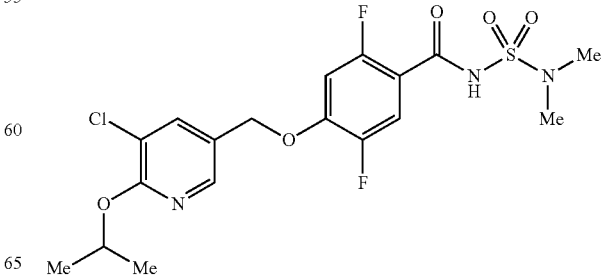

To 4-((5-chloro-6-isopropoxypyridin-3-yl)methoxy)-2,5-difluorobenzoic acid (Preparation 9, 0.05 g, 0.14 mmol) in solution in DCM (5 mL) is added WSCDI (0.04 g, 0.21 mmol), DMAP (0.026 g, 0.21 mmol) and N-ethyl-N-isopropylpropan-2-amine (0.09 mL, 0.42 mmol). After 10 minutes was added N,N-dimethylsulfamide (0.026 g, 0.21 mmol) and the reaction was left at room temperature for 18 hours. The reaction mixture was concentrated in vacuo and purified using reverse phase preparative HPLC to afford the title compound.

LCMS Rt=3.63 minutes MS m/z 462 [M$^{35}$Cl—H]$^-$

EXAMPLE 8

4-[(4-chloro-3-fluorophenoxy)methyl]-N-[(dimethylamino)sulfonyl]-2,5-difluorobenzamide

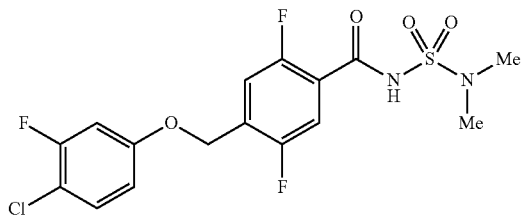 [SMILES: CN(C)S(=O)(=O)NC(=O)c1cc(F)c(COc2ccc(Cl)c(F)c2)cc1F]

To a solution of 4-(bromomethyl)-N-[(dimethylamino)sulfonyl]-2,5-difluorobenzamide (Preparation 1, 33 mg, 0.092 mmol) in DMSO (1 mL) was added 4-chloro-3-fluorophenol (13.5 mg, 0.092 mmol) and K$_2$CO$_3$ (25 mg, 0.18 mmol). The reaction was stirred at room temperature for 3 hours and then at 40° C. for 16 hours. After 16 hours the reaction was diluted with DCM (10 mL) and water (20 mL). The organic was separated and the aqueous was extracted with DCM (2×10 mL). The combined organics were filtered through a phase separation cartridge and reduced to dryness to give a yellow oil which was purified by reverse phase preparative HPLC to afford the title compound.

LCMS Rt=2.36 minutes MS m/z 423 [M$^{35}$ClH]$^+$

EXAMPLE 9

4-[(3-chloro-4-cyanophenoxy)methyl]-N-[(dimethylamino)sulfonyl]-2,5-difluorobenzamide

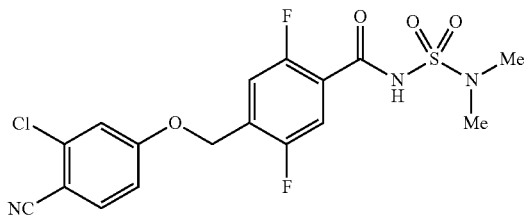 [SMILES: CN(C)S(=O)(=O)NC(=O)c1cc(F)c(COc2ccc(C#N)c(Cl)c2)cc1F]

To a solution of 4-(bromomethyl)-N-[(dimethylamino)sulfonyl]-2,5-difluorobenzamide (Preparation 1, 33 mg, 0.092 mmol) in DMSO (1 mL) was added 2-chloro-4-hydroxybenzonitrile (114 mg, 0.092 mmol) and K$_2$CO$_3$ (25 mg, 0.18 mmol). The reaction was stirred at room temperature for 16 hours. The reaction was diluted with DCM (10 mL) and water (20 mL). The organic layer was separated and the aqueous layer extracted with DCM (2×10 mL). The combined organic layers were filtered through a phase separation cartridge and reduced to dryness to give a yellow oil which was purified by reverse phase preparative HPLC to afford the title compound.

LCMS Rt=2.29 minutes MS m/z 430 [M$^{35}$ClH]$^+$

EXAMPLE 10

4-[(3,4-dichlorophenoxy)methyl]-N-[(dimethylamino)sulfonyl]-2,5-difluorobenzamide

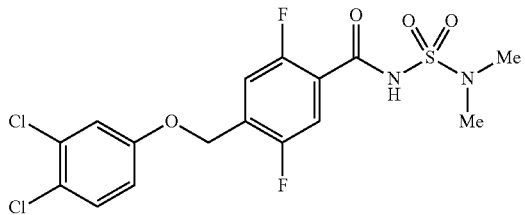 [SMILES: CN(C)S(=O)(=O)NC(=O)c1cc(F)c(COc2ccc(Cl)c(Cl)c2)cc1F]

To a solution of 4-(bromomethyl)-N-[(dimethylamino)sulfonyl]-2,5-difluorobenzamide (Preparation 1, 40 mg, 0.11 mmol) in dimethylsulfoxide (0.5 mL) was added 3,4-dichlorophenol (18 mg, 0.11 mmol) followed by addition of potassium carbonate (31 mg, 0.22 mmol). The reaction was left to stir at room temperature for 18 hours. The reaction mixture was poured into water (50 mL) and acidified with 2M HCl (2 mL), then extracted with EtOAc (2×50 mL). The combined organic layers were washed with water (20 mL), then dried over magnesium sulfate and evaporated in vacuo to give a colourless glass (44 mg). The solid was then triturated with 1:1 ether:heptane (4 mL), sonicated and the supernatant decanted. The resulting solid was dried in vacuo to give an off-white solid as the title compound (47 mg, 98%).

$^1$H NMR (400 MHz, CDCl$_3$): δ 3.05 (s, 6H), 5.18 (s, 2H), 6.80-6.90 (m, 1H), 7.10-7.15 (m, 1H), 7.33-7.45 (m, 2H), 7.80-7.88 (m, 1H), 8.70-8.83 (br s, 1H).

LCMS Rt=1.74 minutes MS m/z 439 [M$^{35}$ClH]$^+$

EXAMPLE 11

4-[(3-chloro-4-fluorophenoxy)methyl]-N-[(dimethylamino)sulfonyl]-2,5-difluorobenzamide

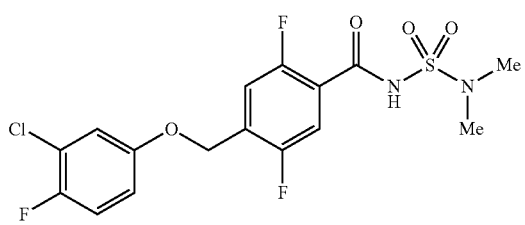 [SMILES: CN(C)S(=O)(=O)NC(=O)c1cc(F)c(COc2ccc(F)c(Cl)c2)cc1F]

A solution of 4-(bromomethyl)-N-[(dimethylamino)sulfonyl]-2,5-difluorobenzamide (Preparation 1, 41.7 mg, 0.117 mmol), 3-chloro-4-fluorophenol (21.7 mg, 0.148 mmol) and potassium carbonate (50.2 mg, 0.363 mmol) in acetone (10 mL) was warmed at 90° C. for 16 hours. The reaction was cooled to room temperature and diluted with ethyl acetate (20 mL), filtered through a plug of Arbocel, and washed with additional ethyl acetate (2×10 mL). The organic filtrate was concentrated in vacuo to afford a clear residue which was dissolved in DMSO (1 mL) and purified using preparative HPLC to afford the title compound as the diethylamine salt (31.5 mg, 64%).

LCMS Rt=3.44 minutes MS m/z 423 [M$^{35}$ClH]$^+$

EXAMPLE 12

4-[(3,4-dichlorobenzyl)oxy]-N-[(dimethylamino)sulfonyl]benzamide

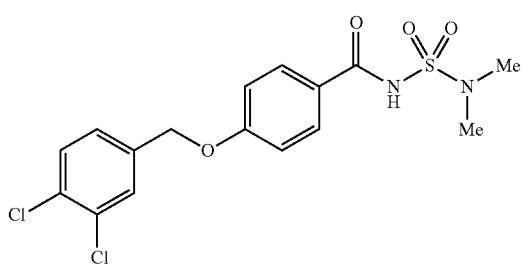 [SMILES: CN(C)S(=O)(=O)NC(=O)c1ccc(OCc2ccc(Cl)c(Cl)c2)cc1]

To a solution of 3,4-dichlorobenzyl alcohol (500 mg, 2.8 mmol) in THF (20 mL) was added sodium hydride (113 mg, 2.8 mmol, 60% dispersion in mineral oil) and stirred at room temperature for 2 hours and then at 50° C. for 30 minutes. Cooled to room temperature and the solvent removed in vacuo to afford an orange solid. This was dissolved in DMSO (5 mL) to which was added a solution of N-[(dimethylamino)sulfonyl]-4-fluorobenzamide (Preparation 11, 580 mg, 2.3 mmol) in DMSO (10 mL) slowly. The dark red solution was heated at 50° C. for 18 h then 120° C. for 2 hours. The mixture was cooled and poured onto water (50 mL) containing 2M HCl (30 mL) and extracted with EtOAc (2×30 mL), washed with 1M HCl (30 mL) and dried over MgSO$_4$, filtered and solvent removed in vacuo to give 1.9 g of crude residue that was purified using reverse phase preparative HPLC to afford the title compound.

LCMS Rt=3.42 minutes MS m/z 403 [M$^{35}$ClH]$^+$

EXAMPLE 13

N-(azetidin-1-ylsulfonyl)-4-{[(5-chloro-6-isopropoxypyridin-3-yl)oxy]methyl}-2,5-difluorobenzamide

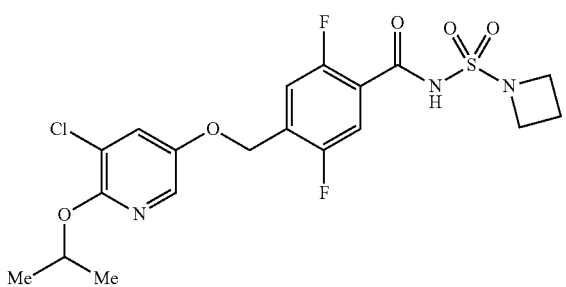 [SMILES: CC(C)Oc1ncc(OCc2cc(F)c(C(=O)NS(=O)(=O)N3CCC3)cc2F)cc1Cl]

To a solution of 4-{[(5-chloro-6-isopropoxypyridin-3-yl)oxy]methyl}-2,5-difluorobenzoic acid (Preparation 15, 100 mg, 0.28 mmol) in dichloromethane (3 mL) was added 1-(3-dimethylaminopropyl)-3-ethylcarbodiimide hydrochloride (80 mg, 0.42 mmol) and 4-dimethylaminopyridine (51 mg, 0.42 mmol). The reaction was allowed to stir at room temperature for 20 minutes, before the addition of azetidine-1-sulfonamide (Preparation 19, 57 mg, 0.42 mmol). The reaction was stirred at room temperature for 18 hours. The solvent was removed in vacuo to leave a yellow solid. The crude material was dissolved in dimethylsulphoxide (2 mL) and purified twice by preparative HPLC to afford the title compound as a white powder (27 mg, 13%).

$^1$H NMR (400 MHz, d$_6$-DMSO): δ 1.20 (s, 6H), 2.10 (m, 2H), 4.00 (m, 4H), 5.10 (m, 1H), 5.20 (s, 2H), 7.60 (m, 1H), 7.70 (m, 1H), 7.90 (s, 1H), 7.95 (s, 1H), 12.05 (br s, 1H).

LCMS Rt=3.62 minutes MS m/z 476 [M$^{35}$ClH]$^+$

EXAMPLE 14

5-chloro-4-{[(5-chloro-6-cyclopropylpyridin-3-yl)oxy]methyl}-N-[(dimethylamino)sulfonyl]-2-fluorobenzamide diethylamine salt

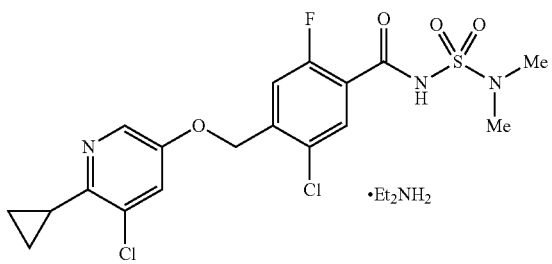 [SMILES: CN(C)S(=O)(=O)NC(=O)c1cc(Cl)c(COc2cnc(C3CC3)c(Cl)c2)cc1F ; "·Et2NH2"]

To a stirred solution of 5-chloro-4-(((5-chloro-6-cyclopropylpyridin-3-yl)oxy)methyl)-2-fluorobenzoic acid (Preparation 27, 200 mg, 0.56 mmol) in dichloromethane (20 mL) was added HATU (256 mg, 0.67 mmol) and diisopropylethylamine (0.30 mL, 1.79 mmol). The reaction mixture was stirred at room temperature for 15 minutes before the addition of N,N-dimethylamino sulphonamide (209 mg, 1.68 mmol). The reaction mixture was stirred under nitrogen at room temperature for 18 hours. Upon completion the reaction mixture was washed with aqueous NH$_4$Cl (15 mL) and brine (15 mL). The organic extracts were dried (MgSO$_4$) and evaporated under vacuum to give the crude product as an orange oil, which was purified by column chromatography on silica (eluting with 1:1 cyclohexane/EtOAc). The partially purified product was dissolved in DMSO (2 mL) and purified by reverse phase chromatography (0-90% acetonitrile/water containing 0.1% formic acid) to afford the title compound as a beige solid (28 mg, 11%).

1H NMR (400 MHz, CD$_3$OD): δ ppm 0.95-0.97 (m, 4H), 1.29 (t, 6H), 2.39-2.46 (m, 1H), 2.81 (s, 6H), 3.03 (q, 4H), 5.20 (s, 2H), 7.32 (d, 1H), 7.49 (d, 1H), 7.75 (d, 1H), 8.13 (d, 1H).

LCMS Rt=3.49 minutes MS m/z=460 [M-H]$^-$

EXAMPLE 15

N-(azetidin-1-ylsulfonyl)-5-chloro-4-{[(5-chloro-6-cyclopropylpyridin-3-yl)oxy]methyl}-2-fluorobenzamide

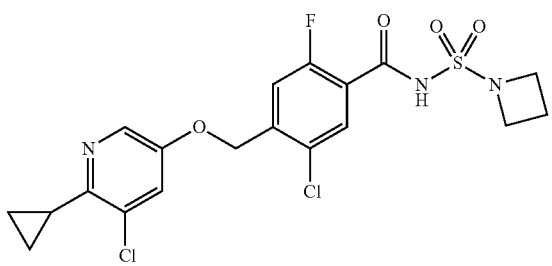 [SMILES: O=C(NS(=O)(=O)N1CCC1)c1cc(Cl)c(COc2cnc(C3CC3)c(Cl)c2)cc1F]

To a stirred solution of 5-chloro-4-(((5-chloro-6-cyclopropylpyridin-3-yl)oxy)methyl)-2-fluorobenzoic acid (Preparation 27, 500 mg, 1.4 mmol) in dichloromethane (40 mL) was added HATU (639 mg, 1.68 mmol) and N,N-diisopropylethylamine (0.78 mL, 4.49 mmol), the mixture was left to stir for 15 minutes. Azetidine-1-sulfonamide (Preparation 19, 573 mg, 4.21 mmol) was added and the reaction mixture was stirred at room temperature for 18 hours. The reaction mixture was then washed with saturated aqueous NH$_4$Cl (30 mL) and brine (30 mL). The organic layer was dried over MgSO$_4$ and evaporated under reduced pressure to give the crude product as an orange oil. This was purified by column chromatography on silica (eluent 1:1 heptane/EtOAc) to give the title compound as an off-white solid (450 mg, 67%).

1H NMR (400 MHz, CDCl$_3$): δ ppm 1.03-0.99 (m, 4H), 2.33-2.26 (m, 2H), 2.46-2.38 (m, 1H), 4.27 (t, 4H), 5.17 (s, 2H), 7.29 (d, 1H), 7.46 (d, 1H), 8.15-8.14 (m, 1H), 8.17 (s, 1H), 8.70 (d, 1H).

LCMS Rt=3.69 minutes MS m/z=474 [M$^+$H]$^+$

EXAMPLE 16

5-chloro-4-{[(5-chloro-6-cyclopropylpyridin-3-yl)oxy]methyl}-N-[(3,3-difluoroazetidin-1-yl)sulfonyl]-2-fluorobenzamide

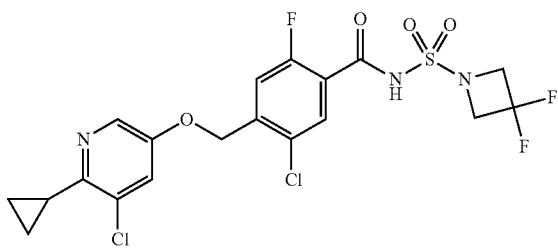 [SMILES: O=C(NS(=O)(=O)N1CC(F)(F)C1)c1cc(Cl)c(COc2cnc(C3CC3)c(Cl)c2)cc1F]

To a solution of 5-chloro-4-(((5-chloro-6-cyclopropylpyridin-3-yl)oxy)methyl)-2-fluorobenzoic acid (Preparation 27, 100 mg, 0.28 mmol) and 3,3-difluoroazetidine-1-sulfonamide (Preparation 23, 75 mg, 0.42 mmol) in DCM (10 mL) was added diisopropylethylamine (73 mg, 0.56 mmol) followed by 1-[bis(dimethylamino)methylene]-1H-1,2,3-triazolo[4,5-b]pyridinium 3-oxid hexafluorophosphate (160 mg, 0.42 mmol). The mixture was stirred at room temperature for 2 hours and concentrated under reduced pressure. The residue was dissolved in DMSO (2 mL) and purified by reverse phase chromatography (0-90% acetonitrile/water containing 0.1% formic acid) to give the title compound as colourless solid (51 mg, 36%).

$^1$H NMR (400 MHz, d$_6$-DMSO): δ 0.89-0.87 (m, 2H), 0.96-0.93 (m, 2H), 2.38-2.33 (m, 1H), 4.57 (t, 4H), 5.25 (s, 2H), 7.63 (d, 1H), 7.70 (d, 1H), 7.85 (d, 1H), 8.24 (d, 1H) ppm.

$^{19}$F NMR (376 MHz, d$_6$-DMSO): δ ppm −98.6, −114.6.

LCMS Rt=3.52 minutes MS m/z=510 [M$^+$H]$^+$

The compounds of formula (I) that follow may be prepared by procedures analogous to those described in the aforementioned Schemes, foregoing Examples 1-16 and the corresponding preparations, or by processes similar to either.

5-chloro-4-{[3-chloro-4-(trifluoromethyl)phenoxy]methyl}-N-[(dimethylamino)sulfonyl]-2-fluorobenzamide;
N-(azetidin-1-ylsulfonyl)-5-chloro-4-{[3-chloro-4-(trifluoromethyl)phenoxy]methyl}-2-fluorobenzamide;
N-(azetidin-1-ylsulfonyl)-4-{[3-chloro-4-(trifluoromethyl)phenoxy]methyl}-2,5-difluorobenzamide;
N-(azetidin-1-ylsulfonyl)-5-chloro-4-[(3,4-dichlorophenoxy)methyl]-2-fluorobenzamide;
N-(azetidin-1-ylsulfonyl)-4-[(3,4-dichlorophenoxy)methyl]-2,5-difluorobenzamide;
4-{[3-chloro-4-(trifluoromethoxy)phenoxy]methyl}-N-[(dimethylamino)sulfonyl]-2,5-difluorobenzamide;
5-chloro-4-({[5-chloro-6-(2,2,3,3,3-pentafluoropropoxy)pyridin-3-yl]oxy}methyl)-N-[(3,3-difluoroazetidin-1-yl)sulfonyl]-2-fluorobenzamide;
5-chloro-4-({[5-chloro-6-(2,2,3,3-tetrafluoropropoxy)pyridin-3-yl]oxy}methyl)-N-[(3,3-difluoroazetidin-1-yl)sulfonyl]-2-fluorobenzamide;
4-({[5-chloro-6-(2,2,2-trifluoro-1,1-dimethylethoxy)pyridin-3-yl]oxy}methyl)-N-[(3,3-difluoroazetidin-1-yl)sulfonyl]-2,5-difluorobenzamide;
4-({[5-chloro-6-(2,2,3,3,3-pentafluoropropoxy)pyridin-3-yl]oxy}methyl)-N-[(3,3-difluoroazetidin-1-yl)sulfonyl]-2,5-difluorobenzamide;
5-chloro-4-({[5-chloro-6-(2,2,3,3-tetrafluoropropoxy)pyridin-3-yl]oxy}methyl)-N-[(dimethylamino)sulfonyl]-2-fluorobenzamide;
N-(azetidin-1-ylsulfonyl)-5-chloro-4-({[5-chloro-6-(2,2,3,3-tetrafluoropropoxy)pyridin-3-yl]oxy}methyl)-2-fluorobenzamide;
5-chloro-4-({[5-chloro-6-(2,2,2-trifluoro-1,1-dimethylethoxy)pyridin-3-yl]oxy}methyl)-N-[(3,3-difluoroazetidin-1-yl)sulfonyl]-2-fluorobenzamide;
N-(azetidin-1-ylsulfonyl)-4-({[5-chloro-6-(2,2,3,3,3-pentafluoropropoxy)pyridin-3-yl]oxy}methyl)-2,5-difluorobenzamide;
4-({[5-chloro-6-(2,2,3,3,3-pentafluoropropoxy)pyridin-3-yl]oxy}methyl)-N-[(dimethylamino)sulfonyl]-2,5-difluorobenzamide;
N-(azetidin-1-ylsulfonyl)-5-chloro-4-({[5-chloro-6-(2,2,3,3,3-pentafluoropropoxy)pyridin-3-yl]oxy}methyl)-2-fluorobenzamide;
5-chloro-4-({[5-chloro-6-(2,2,3,3,3-pentafluoropropoxy)pyridin-3-yl]oxy}methyl)-N-[(dimethylamino)sulfonyl]-2-fluorobenzamide;
N-(azetidin-1-ylsulfonyl)-4-({[5-chloro-6-(2,2,2-trifluoro-1,1-dimethylethoxy)pyridin-3-yl]oxy}methyl)-2,5-difluorobenzamide;
4-({[5-chloro-6-(2,2,2-trifluoro-1,1-dimethylethoxy)pyridin-3-yl]oxy}methyl)-N-[(dimethylamino)sulfonyl]-2,5-difluorobenzamide;
5-chloro-4-({[5-chloro-6-(2,2,2-trifluoroethoxy)pyridin-3-yl]oxy}methyl)-N-[(3,3-difluoroazetidin-1-yl)sulfonyl]-2-fluorobenzamide;
N-(azetidin-1-ylsulfonyl)-5-chloro-4-({[5-chloro-6-(2,2,2-trifluoro-1,1-dimethylethoxy)pyridin-3-yl]oxy}methyl)-2-fluorobenzamide;
5-chloro-4-({[5-chloro-6-(3,3,3-trifluoropropoxy)pyridin-3-yl]oxy}methyl)-N-[(3,3-difluoroazetidin-1-yl)sulfonyl]-2-fluorobenzamide;
5-chloro-4-({[5-chloro-6-(2,2,2-trifluoro-1-methylethoxy)pyridin-3-yl]oxy}methyl)-N-[(dimethylamino)sulfonyl]-2-fluorobenzamide;
4-({[5-chloro-6-(2,2,3,3-tetrafluoropropoxy)pyridin-3-yl]oxy}methyl)-N-[(3,3-difluoroazetidin-1-yl)sulfonyl]-2,5-difluorobenzamide;
N-(azetidin-1-ylsulfonyl)-5-chloro-4-({[5-chloro-6-(2,2,2-trifluoroethoxy)pyridin-3-yl]oxy}methyl)-2-fluorobenzamide;

5-chloro-4-({[5-chloro-6-(3,3,3-trifluoropropoxy)pyridin-3-yl]oxy}methyl)-N-[(dimethylamino)sulfonyl]-2-fluorobenzamide;
N-(azetidin-1-ylsulfonyl)-5-chloro-4-({[5-chloro-6-(2,2,2-trifluoro-1-methylethoxy)pyridin-3-yl]oxy}methyl)-2-fluorobenzamide;
5-chloro-4-({[5-chloro-6-(2,2,2-trifluoro-1-methylethoxy)pyridin-3-yl]oxy}methyl)-N-[(3,3-difluoroazetidin-1-yl)sulfonyl]-2-fluorobenzamide;
5-chloro-4-({[5-chloro-6-(2,2,2-trifluoro-1,1-dimethylethoxy)pyridin-3-yl]oxy}methyl)-N-[(dimethylamino)sulfonyl]-2-fluorobenzamide;
N-(azetidin-1-ylsulfonyl)-5-chloro-4-({[5-chloro-6-(3,3,3-trifluoropropoxy)pyridin-3-yl]oxy}methyl)-2-fluorobenzamide;
4-({[5-chloro-6-(2,2,3,3-tetrafluoropropoxy)pyridin-3-yl]oxy}methyl)-N-[(dimethylamino)sulfonyl]-2,5-difluorobenzamide;
5-chloro-4-({[5-chloro-6-(2,2,2-trifluoroethoxy)pyridin-3-yl]oxy}methyl)-N-[(dimethylamino)sulfonyl]-2-fluorobenzamide;
N-(azetidin-1-ylsulfonyl)-4-({[5-chloro-6-(2,2,3,3-tetrafluoropropoxy)pyridin-3-yl]oxy}methyl)-2,5-difluorobenzamide;
4-{[3-chloro-4-(trifluoromethyl)phenoxy]methyl}-N-[(3,3-difluoroazetidin-1-yl)sulfonyl]-2,5-difluorobenzamide;
N-(azetidin-1-ylsulfonyl)-4-{[4-chloro-3-(trifluoromethoxy)phenoxy]methyl}-2,5-difluorobenzamide;
N-(azetidin-1-ylsulfonyl)-5-chloro-4-{[4-chloro-3-(trifluoromethoxy)phenoxy]methyl}-2-fluorobenzamide;
4-[(3,4-dichlorophenoxy)methyl]-N-[(3,3-difluoroazetidin-1-yl)sulfonyl]-2,5-difluorobenzamide;
5-chloro-4-{[3-chloro-4-(trifluoromethyl)phenoxy]methyl}-N-[(3,3-difluoroazetidin-1-yl)sulfonyl]-2-fluorobenzamide;
N-(azetidin-1-ylsulfonyl)-4-{[3-chloro-4-(trifluoromethyl)phenoxy]methyl}-2,5-difluorobenzamide;
4-{[4-chloro-3-(trifluoromethoxy)phenoxy]methyl}-N-[(3,3-difluoroazetidin-1-yl)sulfonyl]-2,5-difluorobenzamide;
5-chloro-4-[(3,4-dichlorophenoxy)methyl]-N-[(3,3-difluoroazetidin-1-yl)sulfonyl]-2-fluorobenzamide;
5-chloro-4-{[4-chloro-3-(trifluoromethoxy)phenoxy]methyl}-N-[(3,3-difluoroazetidin-1-yl)sulfonyl]-2-fluorobenzamide;
5-chloro-4-[(3,4-dichlorophenoxy)methyl]-N-[(dimethylamino)sulfonyl]-2-fluorobenzamide;
4-{[4-chloro-3-(trifluoromethoxy)phenoxy]methyl}-N-[(dimethylamino)sulfonyl]-2,5-difluorobenzamide;
N-(azetidin-1-ylsulfonyl)-5-chloro-4-{[3-chloro-4-(trifluoromethoxy)phenoxy]methyl}-2-fluorobenzamide;
4-{[4-chloro-3-(trifluoromethyl)phenoxy]methyl}-N-[(3,3-difluoroazetidin-1-yl)sulfonyl]-2,5-difluorobenzamide;
4-{[3-chloro-4-(trifluoromethoxy)phenoxy]methyl}-N-[(3,3-difluoroazetidin-1-yl)sulfonyl]-2,5-difluorobenzamide;
5-chloro-4-{[4-chloro-3-(trifluoromethoxy)phenoxy]methyl}-N-[(dimethylamino)sulfonyl]-2-fluorobenzamide;
N-(azetidin-1-ylsulfonyl)-4-{[4-chloro-3-(trifluoromethyl)phenoxy]methyl}-2,5-difluorobenzamide;
N-(azetidin-1-ylsulfonyl)-5-chloro-4-{[4-chloro-3-(trifluoromethyl)phenoxy]methyl}-2-fluorobenzamide;
5-chloro-4-{[4-chloro-3-(trifluoromethyl)phenoxy]methyl}-N-[(dimethylamino)sulfonyl]-2-fluorobenzamide;
5-chloro-4-{[3-chloro-4-(trifluoromethoxy)phenoxy]methyl}-N-[(3,3-difluoroazetidin-1-yl)sulfonyl]-2-fluorobenzamide;
5-chloro-4-{[4-chloro-3-(trifluoromethyl)phenoxy]methyl}-N-[(3,3-difluoroazetidin-1-yl)sulfonyl]-2-fluorobenzamide; and
5-chloro-4-{[3-chloro-4-(trifluoromethoxy)phenoxy]methyl}-N-[(dimethylamino)sulfonyl]-2-fluorobenzamide.

PREPARATION 1

4-(Bromomethyl)-N-[(dimethylamino)sulfonyl]-2,5-difluorobenzamide

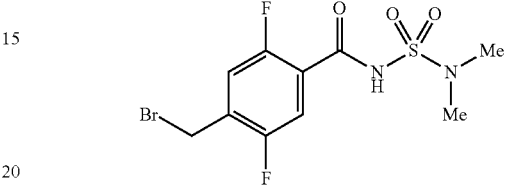

A mixture of N-[(dimethylamino)sulfonyl]-2,5-difluoro-4-methylbenzamide (Preparation 2, 0.50 g, 1.80 mmol), N-bromosuccinimide (freshly recrystallised and dried, 0.42 g, 2.34 mmol) and azobisisobutyronitrile (14.8 mg, 0.09 mmol) in 1,2-dichloroethane (15 mL) was heated under reflux with stirring whilst being irradiated with light from a 100 watt lamp. After 6 hours more N-bromosuccinimide (300 mg, 1.69 mmol) and azobisisobutyronitrile (10 mg, 0.06 mmol) were added and the mixture heated for a further 4 hours. An additional amount of N-bromosuccinimide (100 mg, 0.56 mmol) was then added and the mixture heated under reflux for a further 4 hours. The reaction mixture was cooled to room temperature and evaporated in vacuo to leave a pale yellow oil (0.54 g). Purification by silica gel column chromatography eluting with ethyl acetate/heptane 0:100-1:4 afforded the title compound (0.176 g, 27%) as a colourless oil which solidified on standing.

$^1$H NMR (400 MHz, CDCl$_3$): δ 3.05 (s, 6H), 4.47 (s, 2H), 7.30 (m, 1H), 7.78 (m, 1H), 8.73 (br s, 1H).

LCMS Rt=1.45 minutes MS m/z 355 [M-H]$^-$

PREPARATION 2

N-[(Dimethylamino)sulfonyl]-2,5-difluoro-4-methylbenzamide

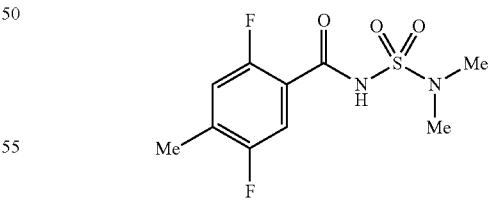

To a suspension of 2,5-difluoro-4-methylbenzoic acid (6.0 g, 3.5 mmol) in 1,2-dichloroethane (100 mL) was added 4-dimethylaminopyridine (10.65 g, 8.7 mmol), 1-ethyl-3-(3-dimethylaminopropyl) carbodiimide:hydrochloride (16.65 g, 8.7 mmol) in 1,2-dichloroethane (60 mL) and N,N-diisopropylethylamine (15 mL, 8.60 mmol) and the mixture stirred at room temperature for 20 minutes. N,N-Dimethylsulfamide (8.64 g, 6.9 mmol) was added to the solution and the mixture heated at 60° C. under nitrogen. After 3 hours the mixture was cooled to room temperature and extracted with dichloromethane (100 mL). The extract was washed successively with 2M hydrochloric acid (2×300 mL), brine (100 mL), dried over magnesium sulfate, filtered and evaporated to afford an oil (8.40 g) which solidified at room temperature. The crude product was purified by silica gel column chromatography eluting with ethyl acetate/heptane 1:4 as eluent to afford the title compound (7.17 g, 79%) as a white solid.

¹H NMR (400 MHz, CDCl₃): δ 2.32 (s, 3H), 3.01 (s, 6H), 7.01 (dd, 1H), 7.65 (dd, 1H), 8.74 (br s, 1H).

LCMS Rt=2.10 minutes MS m/z 277 [M-H]⁻

PREPARATION 3

N-[(Dimethylamino)sulfonyl]-2,4,5-triifluorobenzamide

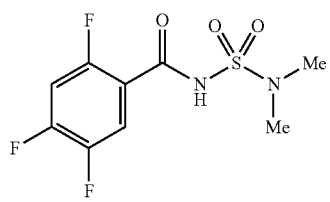 [SMILES: CN(C)S(=O)(=O)NC(=O)c1cc(F)c(F)cc1F]

To a solution of 2,4,5-trifluorobenzoic acid (5 g, 28.4 mmol) in dichloromethane (50 mL) was added 1-ethyl-3-(3-dimethylaminopropyl) carbodiimide (6.53 g, 42.6 mmol) and triethylamine (8.64 g, 11.9 mL, 85.2 mmol). After 15 minutes N,N-dimethylsulfamide (5.3 g, 56.8 mmol) was added followed by 4-dimethylaminopyridine (347 mg, 2.8 mmol). The resulting mixture was allowed to stir at room temperature for 18 hours. The solvent was evaporated and the residue was partitioned between ethyl acetate (50 mL) and 2M HCl (150 mL). The aqueous phase was separated and extracted with ethyl acetate (2×50 mL). The combined organic extracts were dried over magnesium sulfate, filtered, evaporated and the residue purified by reverse-phase chromatography using a gradient of acetonitrile+0.1% formic acid to 100% acetonitrile to yield the title compound (993 mg, 31%) as a white solid.

¹H NMR (400 MHz, CDCl₃): δ 3.02 (s, 6H), 7.08 (dd, 1H), 7.92 (dd, 1H), 8.60-8.80 (br s, 1H).

LCMS Rt=2.60 minutes MS m/z 281 [M-H]⁻

PREPARATION 4

3-Chloro-2-isopropoxypyridine

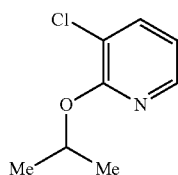 [SMILES: CC(C)Oc1ncccc1Cl]

To a 3-necked flask equipped with a dropping funnel, thermometer and a condenser was added sodium hydride (64.10 g, 1.07 mol) followed by THF (1.65 L). The suspension was cooled to 5° C. and iso-propanol (128 mL, 1.07 mol) was added dropwise over 50 minutes. Upon complete addition the ice bath was removed and the mixture was brought to room temperature and was left to stir for 1 hour. Then 2,3-dichloropyridine (154.6 g, 1.11 mol) was added and the reaction mixture brought to a gentle reflux and left to stir for 18 hours. The reaction mixture was cooled to 5-10° C. and was carefully quenched with brine:water mixture (50:50, 100 mL) followed by water (300 mL). The aqueous layer was extracted with ethyl acetate (3×600 mL), the organic layers combined and washed with brine, dried (MgSO₄), filtered and evaporated to afford the title compound as a dark red oil (164.1 g, 89%).

¹H NMR (400 MHz, CDCl₃): δ 1.40 (d, 6H), 5.36 (m, 1H), 6.80 (m, 1H), 7.6 (m, 1H), 8.05 (m, 1H).

LCMS Rt=3.09 minutes MS m/z 130 [M-iPrH]⁺

PREPARATION 5

3-Chloro-2-isopropoxy-5-(4,4,5,5-tetramethyl-1,3,2-dioxaborolan-2-yl)pyridine

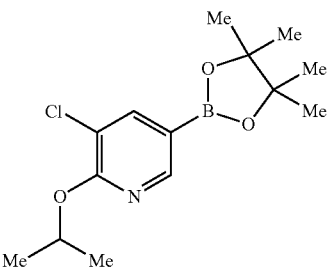 [SMILES: CC(C)Oc1ncc(B2OC(C)(C)C(C)(C)O2)cc1Cl]

A round bottom flask was charged with 3-chloro-2-isopropoxypyridine (Preparation 4, 154.1 g, 897.9 mmol), bispinacolatodiboron (273.6 g, 1.077 mol) and 4,4-di-tert-butyl-2,2-dipyridyl (2.45 g, 8.97 mmol) in heptane (1.55 L). The reaction mixture was degassed 6 times over 15 minutes. Di-μ-methanolatodiiridium(Ir—Ir)-cycloocta-1,5-diene (1:2) (2.45 g; 4.49 mmol) was added and the reaction left to stir for 18 hours under nitrogen. The reaction mixture was cooled to 5° C. and quenched with methanol (70 mL). After complete addition, the reaction mixture was evaporated to dryness and the resulting red viscous oil was used in the next step without further purification.

¹H NMR (400 MHz, CDCl₃): δ 1.20 (d, 6H), 1.30-1.35 (s, 12H), 4.40 (m, 1H), 7.96 (m, 1H), 8.38 (m, 1H).

LCMS Rt=4.55 minutes

PREPARATION 6

5-chloro-6-isopropoxypyridin-3-ol

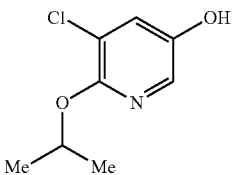 [SMILES: CC(C)Oc1ncc(O)cc1Cl]

To a solution of 3-chloro-2-isopropoxy-5-(4,4,5,5-tetramethyl-1,3,2-dioxaborolan-2-yl)pyridine (Preparation 5, 297.6 g, 897.9 mmol) in acetic acid:water (2.2 L:1.0 L) at 0° C. was added peracetic acid (191 mL; 1.077 mol) and the reaction was allowed to warm gradually to room temperature. After 4 hours the reaction was complete and was quenched with 0.5 M aqueous solution of sodium thiosulfate (225 mL). The resulting dark solution was evaporated to dryness and the residue was passed through a plug of silica eluting with heptanes:ethyl acetate 1:0 to 10:1 to afford a pale yellow viscous oil which contained 8% of the 4-isomer. Further silica gel column chromatography was performed eluting with EtOAc:heptane 1:4 to afford a pale yellow solid which was triturated with heptanes and dried under suction to afford the title compound as a white solid (110 g, 65% over two steps).

$^1$H NMR (400 MHz, CDCl$_3$): δ 1.38 (d, 6H), 4.20 (m, 1H), 7.25 (m, 1H), 7.70 (m, 1H).

LCMS Rt=2.15 minutes MS m/z 186 [MH]$^+$

PREPARATION 7 tert-butyl 4-((5,6-dichloropyridin-3-yl)methoxy)-2,5-difluorobenzoate

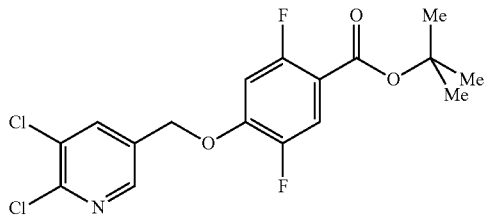 [SMILES: CC(C)(C)OC(=O)c1cc(F)c(OCc2cnc(Cl)c(Cl)c2)cc1F]

Potassium carbonate (535 mg, 3.88 mmol) was added to a solution of tert-butyl 2,4,5-trifluorobenzoate (Preparation 10, 275 mg, 1.29 mmol) and (5,6-dichloropyridin-3-yl)methanol (241 mg, 1.36 mmol) in DMSO (5 mL). The reaction mixture was stirred at RT for 18 hours. After cooling the reaction mixture was quenched with water (25 mL) and extracted with ethyl acetate (2×50 mL). The combined organic layers were washed with water (2×100 mL) and dried over MgSO$_4$, filtered and concentrated in vacuo to give 490 mg of the title compound in a quantitative yield. The crude compound was used without further purification.

$^1$H NMR (400 MHz, d$_6$-DMSO): δ 1.50 (s, 9H), 5.30 (s, 2H), 7.35 (s, 1H), 7.60 (s, 1H), 8.25 (s, 1H), 8.50 (s, 1H).

LCMS Rt=3.95 minutes MS m/z 388 [M$^{35}$Cl—H]$^-$

PREPARATION 8

4-((5,6-dichloropyridin-3-yl)methoxy)-2,5-difluorobenzoic acid

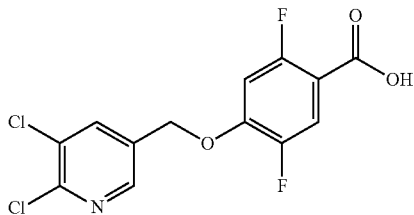 [SMILES: O=C(O)c1cc(F)c(OCc2cnc(Cl)c(Cl)c2)cc1F]

To a solution of tert-butyl 4-((5,6-dichloropyridin-3-yl)methoxy)-2,5-difluorobenzoate (Preparation 7, 0.49 g, 1.26 mmol) in dichloromethane (10 mL) was added trifluoroacetic acid (5 mL). The reaction mixture was stirred 18 hours at room temperature and the reaction mixture was concentrated in vacuo. The crude material was purified by preparative reverse phase column chromatography to afford the title compound as a white solid (210 mg, 50%).

$^1$H NMR (400 MHz, d$_6$-DMSO): δ 5.30 (s, 2H), 7.40 (s, 1H), 7.65 (s, 1H), 8.25 (s, 1H), 8.50 (s, 1H).

LCMS Rt=2.78 minutes MS m/z 332 [M-H]$^-$

PREPARATION 9

4-((5-chloro-6-isopropoxypyridin-3-yl)methoxy)-2,5-difluorobenzoic acid

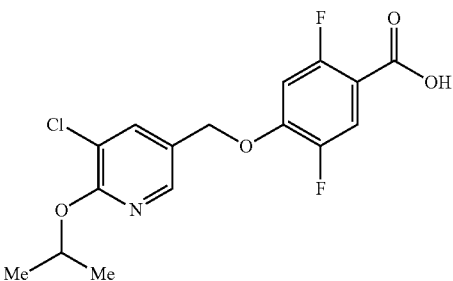 [SMILES: CC(C)Oc1ncc(COc2cc(F)c(C(=O)O)cc2F)cc1Cl]

To a 4-((5,6-dichloropyridin-3-yl)methoxy)-2,5-difluorobenzoic acid (Preparation 8, 210 mg, 0.63 mmol) in THF (5 mL) was added at room temperature sodium hydride (157 mg, 6.3 mmol) followed by iPrOH (5 ml). The reaction mixture was stirred at 90° C. for 18 hours. After cooling, HCl 1M (30 mL) was added to the reaction mixture and it was extracted with ethyl acetate (2×100 mL). The combined organic layers were concentrated in vacuo and purified by reverse phase chromatography to give the title compound (105 mg, 46%).

$^1$H NMR (400 MHz, d$_6$-DMSO): δ 1.35 (m, 6H), 5.20 (m, 1H), 5.30 (s, 2H), 7.40 (s, 1H), 7.60 (s, 1H), 8.00 (s, 1H), 8.25 (s, 1H).

LCMS Rt=3.77 minutes MS m/z 356 [M$^{35}$Cl—H]$^-$

PREPARATION 10 tert-Butyl 2,4,5-trifluorobenzoate

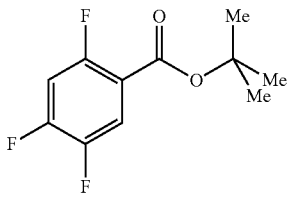 [SMILES: CC(C)(C)OC(=O)c1cc(F)c(F)cc1F]

2,4,5-Trifluorobenzoic acid (10.0 g, 56.8 mmol) was dissolved in tert-butanol (280 mL). Di-tert-butyl dicarbonate (24.8 g, 114 mmol) was added portionwise followed by DMAP (0.694 g, 5.68 mmol) and the mixture stirred at 30° C. under nitrogen for 16 hours. EtOAc (400 mL) was added and the mixture washed with an aqueous solution of HCl (1.0 M, 2×50 mL), then with a saturated aqueous solution of sodium hydrogen carbonate (2×50 mL), and finally with brine (2×50 mL). The organic layer was dried over sodium sulfate, filtered, and concentrated in vacuo to afford the title compound as a colourless oil (12.31 g, 93%).

¹H NMR (400 MHz, CDCl₃): δ 1.58 (s, 9H), 6.93-6.99 (m, 1H), 6.68-6.74 (m, 1H).

PREPARATION 11

N-[(dimethylamino)sulfonyl]-4-fluorobenzamide

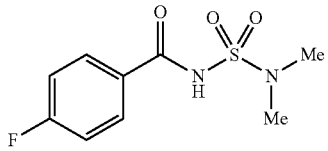 [SMILES: CN(C)S(=O)(=O)NC(=O)c1ccc(F)cc1]

To a solution of 4-fluorobenzoic acid (700 mg, 5.0 mmol) in 1,2-dichloroethane (30 mL) was added EDCI (2.38 g, 12.5 mmol), DMAP (1.52 mg, 12.5 mmol) and N,N-diisopropylethylamine (2.17 mL, 12.5 mmol) and stirred for 20 minutes at room temperature. N,N-dimethylaminosulfonamide (1.24 g, 10.0 mmol) was added to the solution and the mixture heated at 60° C. for 2.5 hours. The mixture was cooled, diluted with water (20 mL) and 2M HCl (20 mL) and extracted with DCM (3×30 mL), washed with water (20 mL) and dried over MgSO₄. The solvent was removed in vacuo to afford the title compound as a white solid (585 mg, 47%). No further purification was necessary.

¹H NMR (400 MHz, CDCl₃) δ ppm 3.02 (s, 6H), 7.15 (dd, 2H), 7.90 (dd, 2H).

¹⁹F NMR (400 MHz, CDCl₃) δ ppm -104 (s, 1F).

LCMS Rt=2.35 minutes MS m/z 247 [MH]+

PREPARATION 12

Ethyl 2,5-difluoro-4-methylbenzoate

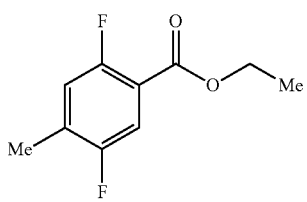 [SMILES: CCOC(=O)c1cc(F)c(C)cc1F]

To a solution of 2,5-difluoro-4-methylbenzoic acid (595 mg, 3.89 mmol) in ethanol (30 mL) was added a catalytic amount of thionyl chloride (2 drops). The reaction was stirred for 18 hours at 70° C., and cooled to room temperature. The solvent was removed in vacuo to afford the title compound as a clear oil (500 mg, 86%). No further purification undertaken.

¹H NMR (400 MHz, CDCl₃): δ 1.30 (t, 3H), 2.30 (s, 3H), 4.40 (q, 2H), 6.90 (m, 1H), 7.60 (m, 1H).

LCMS Rt=3.53 minutes MS no mass ion observed.

PREPARATION 13

Ethyl 4-(bromomethyl)-2,5-difluorobenzoate

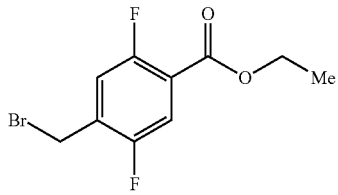

To a solution of ethyl 2,5-difluoro-4-methylbenzoate (Preparation 12, 450 mg, 2.25 mmol) in dichloroethane (10 mL) was added N-bromosuccinimide (520 mg, 2.92 mmol) followed by benzoyl peroxide (54 mg, 0.025 mmol). The reaction was heated at 70° C. for 5 hours then benzoyl peroxide (54 mg, 0.025 mmol) followed by N-bromosuccinimide were added. The reaction was heated at 70° C. for 3 days, then an aqueous solution of sodium thiosulfate (10 mL) and water (30 mL) were added. The organic phase was extracted with dichloromethane (3×20 mL) and the combined organic phases were washed with brine (20 mL), dried over magnesium sulfate, filtered and concentrated in vacuo to afford a light yellow oil. The oil was dissolved in ethyl acetate (7 mL) and N,N-diisopropylethylamine (0.39 mL, 2.25 mmol) was added. The solution was cooled to 0° C. in an ice bath and diethyl phosphate (2.25 mmol, 0.22 mL) was added dropwise. The reaction was stirred at 0° C. for 2 hours before the addition of an aqueous solution of hydrochloric acid (2M, 3 mL). The organic phase was extracted with ethyl acetate (3×10 mL), and the combined organic phases were washed with brine (20 mL), dried over magnesium sulfate, filtered and the solvent removed in vacuo. The crude compound was purified by silica gel column chromatography eluting with heptane:ethyl acetate (gradient from 98:2 to 80:20) to afford the title compound as a colourless oil (455 mg, 75%).

¹H NMR (400 MHz, CDCl₃): δ 1.15 (t, 3H), 4.15 (q, 2H), 4.40 (s, 2H), 7.05 (m, 1H), 7.60 (m, 1H).

LCMS Rt=3.97 minutes MS No mass ion observed.

PREPARATION 14

Ethyl 4-{[(5-chloro-6-isopropoxypyridin-3-yl)oxy]methyl}-2,5-difluorobenzoate

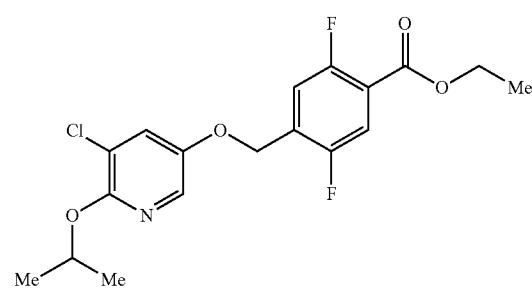 [SMILES: CCOC(=O)c1cc(F)c(COc2cnc(OC(C)C)c(Cl)c2)cc1F]

To a solution of ethyl 4-(bromomethyl)-2,5-difluorobenzoate (Preparation 13, 200 mg, 0.72 mmol) in N,N-dimethylformamide (4 mL) at room temperature under nitrogen was added 5-chloro-6-isopropoxypyridin-3-ol (Preparation 6, 161 mg, 0.86 mmol) and potassium carbonate (198 mg, 1.43 mmol). The reaction was stirred at room temperature for 2 days, then partitioned between water and ethyl acetate (1:1 10 mL). The organic phase was washed with brine (10 mL), dried over magnesium sulfate, filtered and the solvent removed in vacuo to afford the title compound as a light yellow solid (400 mg, >100%). No further purification undertaken.

$^1$H NMR (400 MHz, CDCl$_3$): δ 1.40 (m, 9H), 4.40 (q, 2H), 5.05 (s, 2H), 5.20 (m, 1H), 7.30 (m, 1H), 7.40 (s, 1H), 7.65 (m, 1H), 7.75 (s, 1H).

LCMS Rt=3.99 minutes MS m/z 386 [M$^{35}$ClH]$^+$

PREPARATION 15

4-{[(5-chloro-6-isopropoxypyridin-3-yl)oxy]methyl}-2,5-difluorobenzoic acid

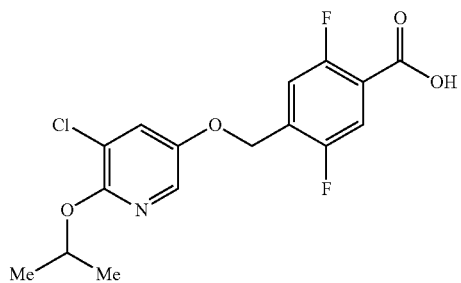 [SMILES: CC(C)Oc1ncc(OCc2cc(F)c(C(=O)O)cc2F)cc1Cl]

To a solution of ethyl 4-{[(5-chloro-6-isopropoxypyridin-3-yl)oxy]methyl}-2,5-difluorobenzoate (Preparation 14, 400 mg, 1.03 mmol) in a mixture tetrahydrofuran/methanol (1/1 10 mL) was added an aqueous solution of sodium hydroxide (2M, 2.6 mL, 5.15 mmol). The reaction was stirred at room temperature for 2 hours and diluted with ethyl acetate (20 mL). An aqueous solution of hydrochloric acid (2M, 10 mL) was added to pH 1. The organic phase was extracted with ethyl acetate (2×10 mL) and the combined organic layers were washed with brine (20 mL), dried over magnesium sulfate, filtered and the solvent removed in vacuo to afford the title compound as a colourless oil (240 mg, 94% over two steps). No further purification undertaken.

$^1$H NMR (400 MHz, d$_6$-DMSO): δ 1.20 (d, 6H), 5.20 (m, 3H), 7.55 (m, 1H), 7.60 (m, 1H), 7.90 (s, 1H), 7.95 (s, 1H), 13.60 (br s, 1H).

LCMS Rt=3.77 minutes MS m/z 358 [M$^{35}$ClH]$^+$

PREPARATION 16

4-{[4-chloro-3-(trifluoromethyl)phenoxy]methyl}benzoic acid

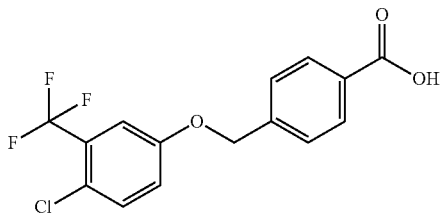 [SMILES: O=C(O)c1ccc(COc2ccc(Cl)c(C(F)(F)F)c2)cc1]

To a solution of ethyl 4-{[4-chloro-3-(trifluoromethyl)phenoxy]methyl}benzoate (Preparation 17, 350 mg, 0.98 mmol) in methanol (8.0 mL) was added water (2 mL) followed by sodium hydroxide (400 mg, 9.8 mmol). The reaction mixture was heated to 55° C. for 3 hours, then cooled and diluted with EtOAc (50 mL) and 2M HCl (50 mL). The aqueous layer was separated and washed with EtOAc (2×50 mL). The combined organic layers were dried over magnesium sulfate, filtered and concentrated in vacuo to yield a white solid as the title compound (276 mg, 86%).

$^1$H NMR (400 MHz, CDCl$_3$): δ 4.99 (s, 2H), 6.92 (dd, 1H), 7.13 (d, 1H), 7.24 (s, 1H), 7.32 (d, 2H), 7.91 (d, 2H).

LCMS Rt=1.76 minutes MS m/z 329 [M$^{35}$Cl—H]$^-$

PREPARATION 17

Ethyl 4-{[4-chloro-3-(trifluoromethyl)phenoxy]methyl}benzoate

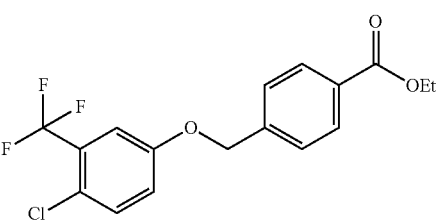 [SMILES: CCOC(=O)c1ccc(COc2ccc(Cl)c(C(F)(F)F)c2)cc1]

To a solution of 4-chloro-3-(trifluoromethyl)phenol (190 mg, 0.97 mmol) in DMSO (5.0 mL) was added potassium carbonate (276 mg, 2.0 mmol). The reaction mixture was stirred at room temperature for 10 minutes, before addition of ethyl 4-(bromomethyl)benzoate (235 mg, 0.97 mmol). The resulting mixture was heated to 70° C. with stirring for 3 hours before cooling back to room temperature. Water (50 mL) and EtOAc (50 mL) were added and the layers partitioned. The aqueous fractions were washed with EtOAc (2×50 mL) and the combined organic layers dried over magnesium sulfate, filtered and concentrated in vacuo to yield a white solid as the title compound (350 mg, 100%).

$^1$H NMR (400 MHz, CDCl$_3$): δ 1.40 (t, 3H), 4.39 (q, 2H), 5.14 (s, 2H), 7.04 (dd, 1H), 7.29 (d, 1H), 7.39 (d, 1H), 7.48 (d, 2H), 8.08 (d, 2H).

LCMS Rt=2.01 minutes MS m/z 359 [M$^{35}$ClH]$^+$

PREPARATION 18

Ethyl 4-{[3-chloro-4-(trifluoromethyl)phenoxy]methyl}benzoate

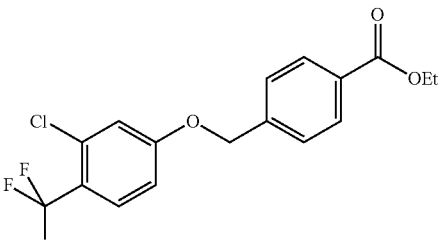

To a solution of 3-chloro-4-(trifluoromethyl)phenol (110 mg, 0.56 mmol) in DMSO (5.0 mL) was added potassium carbonate (155 mg, 1.1 mmol). The reaction mixture was stirred at room temperature for 10 minutes, before addition of ethyl 4-(bromomethyl)benzoate (136 mg, 0.56 mmol). The resulting mixture was heated to 70° C. with stirring for 3 hours before cooling back to room temperature. Water (50 mL) and EtOAc (50 mL) were added and the layers partitioned. The aqueous layers were washed with EtOAc (2×50 mL) and the combined organic layers dried over magnesium sulfate, filtered and concentrated in vacuo to yield a white solid as the title compound (198 mg, 99%).

$^1$H NMR (400 MHz, CDCl$_3$): δ 1.40 (t, 3H), 4.39 (q, 2H), 5.16 (s, 2H), 6.90 (dd, 1H), 7.10 (d, 1H), 7.48 (d, 2H), 7.59 (d, 1H), 8.08 (d, 2H).

LCMS Rt=1.65 minutes no mass ion observed

PREPARATION 19

Azetidine-1-sulfonamide

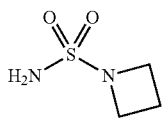

A mixture of palladium hydroxide 20% (350 mg), benzyl (azetidin-1-ylsulfonyl)carbamate (Preparation 20, 1.49 g, 5.5 mmol) and 1-methyl-1,4-cyclohexadiene (10.7 g, 0.11 mol) in methanol (35 mL) was stirred and heated at 60° C. overnight under nitrogen. The reaction mixture was cooled to room temperature, passed through a pad of celite and concentrated in vacuo to afford the title compound (437 mg, 58%) as a solid.

$^1$H NMR (400 MHz, CD$_3$OD) δ ppm 2.15 (pent, 2H), 3.78 (t, 4H).

LCMS no mass ion observed

PREPARATION 20

Benzyl (azetidin-1-ylsulfonyl)carbamate

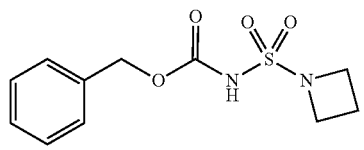 [SMILES: O=C(NS(=O)(=O)N1CCC1)OCc1ccccc1]

Azetidine (0.36 g, 0.5 mmol) was added to N-{1-[N-(benzyloxycarbonyl)-sulfamoyl]pyridin-4(1H)-ylidene}-N-methylmethanaminium chloride (Preparation 21, 2.0 g, 0.5 mmol) in DCM (10 mL). The reaction mixture was stirred overnight at room temperature. The mixture was concentrated in vacuo and the residue partitioned between ethyl acetate (50 mL) and water (50 mL). The organic layer was discarded and the aqueous layer was acidified with 1M HCl. The aqueous layer was extracted with ethylacetate (2×50 mL), dried over magnesium sulfate and concentrated to afford the title compound (1.49 g, 100%).

$^1$H NMR (400 MHz, CDCl$_3$) δ ppm 2.20 (pent, 2H), 4.10 (t, 4H), 5.22 (s, 2H), 7.39 (m, 5H).

LCMS Rt=1.93 minutes MS m/z 271 [MH]$^+$

PREPARATION 21

N-{1-[N-(benzyloxycarbonyl)sulfamoyl]pyridin-4(1H)-ylidene}-N-methylmethanaminium chloride

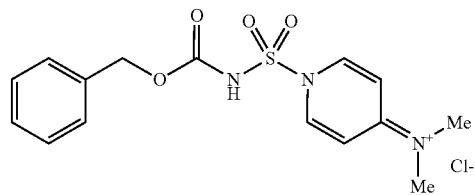 [SMILES: C[N+](C)=c1ccn(S(=O)(=O)NC(=O)OCc2ccccc2)cc1 ; [Cl-]]

Chlorosulfonylisocyanate (5.85 mL, 67.0 mmol) was added slowly over 20 min, to a stirred solution of benzylalcohol (7.05 g, 67.0 mmol) in DCM (80 mL) at 0° C. After 30 min DMAP (16.5 g, 0.13 mol) was added portion-wise, keeping the temperature between 0 and 5° C. The reaction was allowed to warm to room temperature over 3 hours. Water (40 mL) was added carefully to the mixture and the layer separated. The organic layer was washed with water (40 mL), dried over magnesium sulfate, filtered and concentrated in vacuo to yield a solid. The solid was recrystallized from acetonitrile (150 mL) to provide the title compound (11.9 g, 55%) as a white solid.

$^1$H NMR (400 MHz, CD$_3$OD) δ ppm 3.25 (s, 6H), 4.95 (s, 2H), 6.84 (d, 2H), 7.31 (m, 5H), 8.48 (d, 2H).

LCMS Rt=1.60 minutes MS m/z 336 [M-$^{35}$Cl]$^+$

PREPARATION 22 benzyl (3,3-difluoroazetidin-1-yl)sulfonylcarbamate

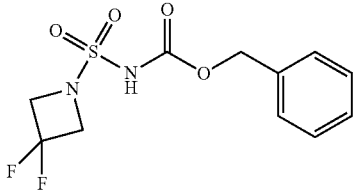 [SMILES: O=C(NS(=O)(=O)N1CC(F)(F)C1)OCc1ccccc1]

To a stirred solution of N-(1-(N-((benzyloxy)carbonyl)sulfamoyl)pyridin-4(1H)-ylidene)-N-methylmethanaminium chloride (Preparation 21, 3.15 g, 8.49 mmol) in CH$_2$Cl$_2$ (15 mL) were added N,N,-diisopropylethylamine (2.19 g, 17.0 mmol) and 3,3-difluoroazetidine hydrochloride (1.10 g, 8.49 mmol). The mixture was stirred at room temperature for 16 hours. The solvent was removed under reduced pressure and the residue diluted with EtOAc (40 mL) and washed with water (40 mL). The aqueous washings were acidified with 2M aqueous solution of HCl and extracted with EtOAC (2×40 mL), the combined organic layers were dried over MgSO$_4$ and concentrated to give the title compound as an amber oil (800 mg, 31%).

$^1$H NMR (400 MHz, CDCl$_3$) δ ppm 4.46-4.54 (t, 4H), 5.23 (s, 2H), 7.36-7.42 (m, 5H).

PREPARATION 23

3,3-difluoroazetidine-1-sulfonamide

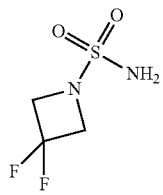

To a solution of benzyl (3,3-difluoroazetidin-1-yl)sulfonylcarbamate (Preparation 22, 800 mg, 2.61 mmol) in methanol (20 mL) was added 10% palladium hydroxide on charcoal (150 mg) and methylcyclohexadiene (4.9 g, 52.3 mmol) and the mixture heated at reflux for 18 hours. Once cooled the reaction mixture was filtered through Celite™ and concentrated to give the title compound as an amber oil (410 mg, 91%).

$^1$H NMR (400 MHz, DMSO-$d_6$) δ ppm 4.15-4.25 (t, 4H), 7.30 (s, 2H).

PREPARATION 24 tert-butyl 5-chloro-2-fluoro-4-methylbenzoate

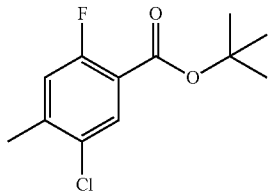 [SMILES: Cc1cc(F)c(C(=O)OC(C)(C)C)cc1Cl]

To a stirred solution of 5-chloro-2-fluoro-4-methylbenzoic acid (5.00 g, 26.9 mmol) in tert-butanol (100 mL) was added di-tert-butyl dicarbonate (17.5 g, 80.7 mmol) followed by DMAP (656 mg, 5.40 mmol). The reaction mixture was stirred under nitrogen at 45° C. for 18 hours. The reaction mixture was concentrated under vacuum and dissolved in EtOAc (50 mL). The organic layer was washed with an aqueous solution of 2 M HCl (50 mL), an aqueous solution of 2M NaOH (50 mL) and brine (50 mL). The organic layer was dried over MgSO$_4$ and concentrated under vacuum to give the crude product as a pale yellow oil. This was purified by filtering through a pad of silica washing with 3:7 EtOAc/cyclohexane to give the title compound as a colourless oil (4.60 g, 71%).

1H NMR (400 MHz, CDCl$_3$): δ ppm 1.59 (s, 9H), 2.39 (s, 3H), 6.98 (d, 1H), 7.81 (d, 1H).

PREPARATION 25 tert-butyl 5-chloro-4-(bromomethyl)-2-fluorobenzoate

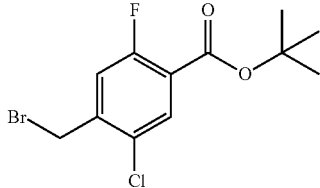 [SMILES: CC(C)(C)OC(=O)c1cc(Cl)c(CBr)cc1F]

To a stirred solution of tert-butyl 5-chloro-2-fluoro-4-methylbenzoate (Preparation 24, 4.60 g, 18.8 mmol) in carbon tetrachloride (60 mL) was added NBS (3.70 g, 20.7 mmol) and dibenzoyl peroxide (228 mg, 0.94 mmol). The resulting mixture was stirred under nitrogen at 85° C. for 18 hours. Additional NBS (7.60 g, 41.4 mmol) was added and the mixture stirred for 4 hours. Further NBS (1.00 g, 5.6 mmol) and dibenzoyl peroxide (200 mg, 0.85 mmol) were then added and the reaction mixture was left to stir under nitrogen at 85° C. for 18 hours. The reaction mixture was then cooled to room temperature and diluted with CH$_2$Cl$_2$ (50 mL). The organic layer was washed with water (50 mL), aqueous sodium thiosulfate solution (50 mL), dried over MgSO$_4$, and concentrated under vacuum to give the crude product as a yellow oil. The crude product was purified by column chromatography on silica (eluent 95:5 heptane/EtOAc) yielding a 2:1 mixture of the title compound (tert-butyl 5-chloro-4-(bromomethyl)-2-fluorobenzoate) and tert-butyl 5-chloro-4-(dibromomethyl)-2-fluorobenzoate (3.96 g). To a stirred solution of the mixture of tert-butyl 5-chloro-4-(bromomethyl)-2-fluorobenzoate and tert-butyl 5-chloro-4-(dibromomethyl)-2-fluorobenzoate in EtOAc (25 mL) were added N,N-diisopropylethylamine (2.60 mL, 14.8 mmol) and diethyl phosphate (1.30 ml, 9.80 mmol) dropwise. The reaction mixture was stirred under nitrogen at room temperature for 18 hours. The reaction mixture was washed with aqueous solution of 1M HCl (30 mL) and brine (30 mL), dried over MgSO$_4$ and concentrated under vacuum to give the crude product as an orange oil. This was purified by column chromatography on silica (eluent 9:1 heptane/EtOAc) yielding the title compound as an orange oil (2.9 g, 48%).

$^1$H NMR (400 MHz, CDCl$_3$): δ ppm 1.58 (s, 9H), 4.51 (s, 2H), 7.22 (d, 1H), 7.86 (d, 1H).

PREPARATION 26 tert-butyl 5-chloro-4-(((5-chloro-6-cyclopropylpyridin-3-yl)oxy)methyl)-2-fluorobenzoate

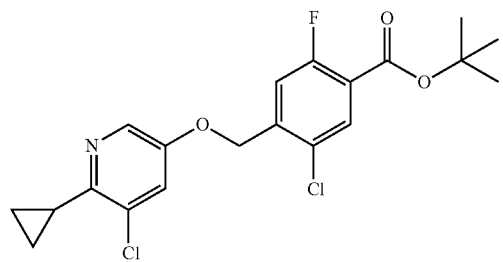 [SMILES: CC(C)(C)OC(=O)c1cc(Cl)c(COc2cnc(C3CC3)c(Cl)c2)cc1F]

To a stirred solution of tert-butyl 4-(bromomethyl)-5-chloro-2-fluorobenzoate (Preparation 25, 2.50 g, 7.99 mmol) and 5-chloro-6-cyclopropylpyridin-3-ol (Preparation 42 WO2012007869, 1.13 g, 6.66 mmol) in DMSO (25 mL) was added K$_2$CO$_3$ (2.76 g, 19.9 mmol). The resulting mixture was stirred under nitrogen at room temperature for 18 hours. The reaction mixture was then quenched with water (30 mL) and extracted with EtOAc (2×30 mL). The combined organic layers were washed with water (30 mL), dried over MgSO$_4$ and evaporated under reduced pressure to give the crude product (2.69 g). Purification was accomplished by column chromatography on silica (eluting with 1:9 Et$_2$O/cyclohexane) affording the title compound (1.24 g, 46%).

1H NMR (400 MHz, CDCl$_3$): δ ppm 0.88-0.93 (m, 4H), 1.53 (s, 9H), 2.32-2.39 (m, 1H), 5.06 (s, 2H), 7.18 (d, 1H), 7.26 (d, 1H), 7.82 (d, 1H), 8.06 (d, 1H).

PREPARATION 27

5-chloro-4-(((5-chloro-6-cyclopropylpyridin-3-yl)oxy)methyl)-2-fluorobenzoic acid

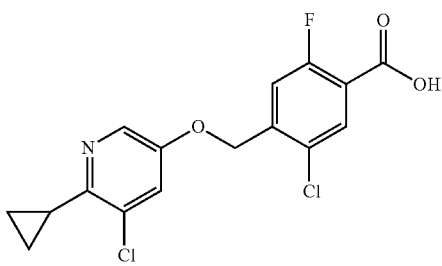 [SMILES: O=C(O)c1cc(Cl)c(COc2cnc(C3CC3)c(Cl)c2)cc1F]

To a stirred solution of tert-butyl 5-chloro-4-(((5-chloro-6-cyclopropylpyridin-3-yl)oxy)methyl)-2-fluorobenzoate (Preparation 26, 1.24 g, 3.01 mmol) in dichloromethane (22 mL) was added TFA (10.0 mL, 0.02 mol). The mixture was stirred under nitrogen at room temperature for 18 hours. Additional TFA (2.50 mL, 32.0 mmol) was added and stirring continued for 3 hours. The reaction mixture was evaporated under reduced pressure and the resulting residue dissolved in EtOAc (25 mL) and washed with 2M aqueous solution of HCl (25 mL). The resulting solid was filtered to afford the title compound (1.4 g, crude quant.) which was used with no further purification.

1H NMR (400 MHz, CDCl$_3$): δ ppm 0.90-0.94 (m, 4H), 4.18-4.27 (m, 1H), 5.21 (s, 2H), 7.42 (m, 1H), 7.67 (m, 1H), 8.09 (d, 1H), 8.48 (s, 1H).

The ability of the compounds of formula (I) to block the Nav1.7 (or SCN9A) channel were measured using the assay described below.

Cell Line Construction and Maintenance

Human Embryonic Kidney (HEK) cells were transfected with an hSCN9A construct using lipofectamine reagent (Invitrogen), using standard techniques. Cells stably expressing the hSCN9A constructs were identified by their resistance to G-418 (400 µg/ml). Clones were screened for expression using the whole-cell voltage-clamp technique.

Cell Culture

HEK cells stably transfected with hSCN9A were maintained in DMEM medium supplemented with 10% heat-inactivated fetal bovine serum and 400 µg/ml G-418 in an incubator at 37° C. with a humidified atmosphere of 10% CO$_2$. For HTS, cells were harvested from flasks by trypsinization and replated in an appropriate multi-well plate (typically 96 or 384 wells/plate) such that confluence would be achieved within 24 hours of plating. For electrophysiological studies, cells were removed from the culture flask by brief trypsinization and re-plated at low density onto glass cover slips. Cells were typically used for electrophysiological experiments within 24 to 72 hours after plating.

Electrophysiological Recording

Cover slips containing HEK cells expressing hSCN9A were placed in a bath on the stage of an inverted microscope and perfused (approximately 1 ml/minutes) with extracellular solution of the following composition: 138 mM NaCl, 2 mM CaCl$_2$, 5.4 mM KCl, 1 mM MgCl$_2$, 10 mM glucose, and 10 mM HEPES, pH 7.4, with NaOH. Pipettes were filled with an intracellular solution of the following composition: 135 mM CsF, 5 mM CsCl, 2 mM MgCl$_2$, 10 mM EGTA, 10 mM HEPES, pH 7.3 with NaOH, and had a resistance of 1 to 2 megaohms. The osmolarity of the extracellular and intracellular solutions was 300 mOsm/kg and 295 mOsm/kg, respectively. All recordings were made at room temperature (22-24° C.) using AXOPATCH 200B amplifiers and PCLAMP software (Axon Instruments, Burlingame, Calif.).

hSCN9A currents in HEK cells were measured using the whole-cell configuration of the patch-clamp technique (Hamill et al., 1981). Uncompensated series resistance was typically 2 to 5 mega ohms and >85% series resistance compensation was routinely achieved. As a result, voltage errors were negligible and no correction was applied. Current records were acquired at 20 to 50 KHz and filtered at 5 to 10 KHz.

HEK cells stably transfected with hSCN9A were viewed under Hoffman contrast optics and placed in front of an array of flow pipes emitting either control or compound-containing extracellular solutions. All compounds were dissolved in dimethyl sulfoxide to make 10 mM stock solutions, which were then diluted into extracellular solution to attain the final concentrations desired. The final concentration of dimethyl sulfoxide (<0.3% dimethyl sulfoxide) was found to have no significant effect on hSCN9A sodium currents. The voltage-dependence of inactivation was determined by applying a series of depolarizing prepulses (8 sec long in 10 mV increments) from a negative holding potential. The voltage was then immediately stepped to 0 mV to assess the magnitude of the sodium current. Currents elicited at 0 mV were plotted as a function of prepulse potential to allow estimation of the voltage at which 50% of the channels were inactivated (midpoint of inactivation or V1/2). Compounds were tested for their ability to inhibit hSCN9A sodium channels by activating the channel with a 20 msec voltage step to 0 mV following an 8 second conditioning prepulse to the empirically determined V1/2. Compound effect (% inhibition) was determined by difference in current amplitude before and after application of test compounds. For ease of comparison, "estimated IC-50" (EIC$_{50}$) values were calculated from single point electrophysiology data by the following equation, (tested concentration, uM)×(100−% inhibition/% inhibition). Inhibition values <20% and >80% were excluded from the calculation.

Electrophysiological assays were conducted with PatchXpress 7000 hardware and associated software (Molecular Devices Corp). All assay buffers and solutions were identical to those used in conventional whole-cell voltage clamp experiments described above. hSCN9A cells were grown as above to 50%-80% confluency and harvested by trypsinization. Trypsinized cells were washed and resuspended in extracellular buffer at a concentration of 1×10$^6$ cells/ml. The onboard liquid handling facility of the PatchXpress was used for dispensing cells and application of test compounds. Determination of the voltage midpoint of inactivation was as described for conventional whole-cell recordings. Cells were then voltage-clamped to the empirically determined V1/2 and current was activated by a 20 msec voltage step to 0 mV.

Electrophysiological assays may also be conducted using the Ionworks Quattro automated electrophysiological platform (Molecular Devices Corp). Intracellular and extracellular solutions were as described above with the following changes, 100 µg/ml amphotericin was added to the intracellular solution to perforate the membrane and allow electrical access to the cells. hSCN9A cells were grown and harvested as for PatchXpress and cells were resuspended in extracellular solution at a concentration of 3-4×10$^6$ cells/ml. The onboard liquid handling facility of the Ionworks Quattro was used for dispensing cells and application of test compounds. A voltage protocol was then applied that comprised of a voltage step to fully inactivate the sodium channels, followed by a brief hyperpolarized recovery period to allow partial recovery from inactivation for unblocked sodium channels, followed by a test depolarized voltage step to assess magnitude of inhibition by test compound. Compound effect was determined based on current amplitude difference between the pre-compound addition and post-compound addition scans.

Compounds of the Examples were tested in the assay described above using the PatchXpress platform and found to have the Nav1.7 $EIC_{50}$ (uM) values specified in the table below.

| Ex. | $EIC_{50}$ |
|---|---|
| 1 | 0.24 |
| 2 | 0.11 |
| 3 | 1.3 |
| 4 | 1.5 |
| 5 | 0.92 |
| 6 | 0.20 |
| 7 | 8.3 |
| 8 | 0.85 |
| 9 | >3 |
| 10 | 0.35 |
| 11 | 0.58 |
| 12 | 2.3 |
| 13 | 0.15 |
| 14 | 0.42 |
| 15 | 0.09 |
| 16 | 0.27 |

The ability of compounds of formula (I) to block the Nav1.5 (or SCN5A) channel can also be measured using an assay analogous to that described above but replacing the SCN9A gene with the SCN5A gene. All other conditions remain the same including the same cell line and conditions for cell growth. The estimated IC50s are determined at the half inactivation for Nav1.5. These results can be compared to the $EIC_{50}$ value at the Nav1.7 channel to determine the selectivity of a given compound for Nav1.7 vs Nav1.5.

The invention claimed is:
1. A compound of formula (I):

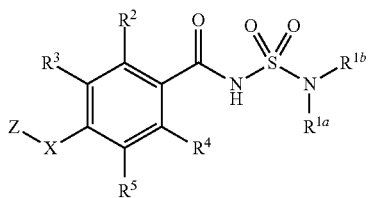

(I)

or a pharmaceutically acceptable salt thereof, wherein
X is —$OCH_2$— or —$CH_2O$—;
Z is selected from naphthyl, phenyl or $Het^1$, wherein said naphthyl, phenyl or $Het^1$ is optionally substituted by one to three substituents selected from $Y^1$ or $Y^2$; wherein $Y^1$ and $Y^2$ are each independently selected from:
  (i) F;
  (ii) Cl;
  (iii) CN;
  (iv) ($C_1$-$C_8$)alkyl, optionally substituted by ($C_3$-$C_8$)cycloalkyl and/or, by one to eight F;
  (v) ($C_3$-$C_8$)cycloalkyl, optionally substituted by one to eight F;
  (vi) $NR^7R^8$;
  (vii) ($C_1$-$C_8$)alkyloxy, optionally substituted by one to three $R^9$, and/or, by one to eight F;
  (viii) ($C_3$-$C_8$)cycloalkyloxy, optionally substituted by one to eight F and/or by one to three $R^{10}$, and further optionally fused to a phenyl ring;
  (ix) phenyl, optionally substituted by one to three substituents selected from F or $R^{10}$;
  (x) phenoxy, optionally substituted by one to three substituents selected from F or $R^{10}$;
  (xi) $Het^2$;
  (xii) $Het^2$-oxy; or
  (xiii) $Het^3$;
$R^{1a}$ and $R^{1b}$ are each independently selected from:
  (i) H,
  (ii) ($C_1$-$C_6$)alkyl; or
  (iii) ($C_3$-$C_6$)cycloalkyl, optionally substituted by one to eight F or, $R^{1a}$ and $R^{1b}$ taken together with the N atom to which they are attached, form a 3- to 8-membered monoheterocycloalkyl, said monoheterocycloalkyl being optionally substituted on a ring carbon atom by one to eight F;
$R^2$, $R^3$, and $R^4$ are each independently selected from H, F, Cl or —$OCH_3$;
$R^5$ is H, CN, F, Cl, $Het^3$, or $R^6$; wherein $R^6$ is selected from ($C_1$-$C_6$)alkyl or ($C_1$-$C_6$)alkyloxy, and said ($C_1$-$C_6$)alkyl and ($C_1$-$C_6$)alkyloxy are optionally substituted by one to eight F;
$R^7$ and $R^8$ are each independently selected from:
  (i) H;
  (ii) ($C_1$-$C_8$)alkyl, optionally substituted by one to three $R^{11}$;
  (iii) ($C_3$-$C_8$)cycloalkyl, optionally substituted by one to eight F and/or by one to three $R^{10}$, and further optionally fused to a phenyl ring;
  (iv) 'C-linked' $Het^2$; or
  (v) C-linked $Het^3$;
$R^9$ is selected from:
  (i) ($C_1$-$C_6$)alkyloxy;
  (ii) ($C_3$-$C_8$)cycloalkyl, optionally substituted by one to eight F;
  (iii) $Het^2$; or
  (iv) phenyl, optionally substituted by one to three $R^6$;
$R^{10}$ is Cl, CN or $R^6$;
$R^{11}$ is selected from:
  (i) F;
  (ii) ($C_1$-$C_6$)alkyloxy;
  (iii) ($C_3$-$C_8$)cycloalkyl, optionally substituted by one to eight F;
  (iv) 'C-linked' $Het^2$; or
  (v) phenyl, optionally substituted by one to three $R^6$;
$Het^1$ is a 6-, 9- or 10-membered heteroaryl containing one to three nitrogen atoms;
$Het^2$ is a 3- to 8-membered saturated monoheterocycloalkyl containing one or two ring members selected from —$NR^{12}$— and —O—, said monoheterocycloalkyl being optionally substituted on a ring carbon atom by one to three substituents independently selected from F, ($C_1$-$C_6$)alkyl, ($C_1$-$C_4$)alkyloxy($C_0$-$C_4$)alkylene or ($C_3$-$C_8$)cycloalkyl;
$Het^3$ is a 5- or 6-membered heteroaryl containing one to three nitrogen atoms, said heteroaryl being optionally substituted by one to three substituents selected from F, Cl, CN or $R^6$; and $R^{12}$ is H, $(C_1-C_6)$alkyl or $(C_3-C_8)$cycloalkyl, wherein said $(C_1-C_6)$alkyl and said $(C_3-C_8)$cycloalkyl are optionally substituted by one to eight F; or, when $Het^2$ is 'N-linked', $R^{12}$ is absent.

2. The compound according to claim 1, or a pharmaceutically acceptable salt thereof wherein X is —$OCH_2$—.

3. The compound according to claim 1, or a pharmaceutically acceptable salt thereof wherein X is —$CH_2O$—.

4. The compound according claim 1, or a pharmaceutically acceptable salt thereof wherein Z is phenyl optionally substituted by one to three substituents selected from $Y^1$ and $Y^2$.

5. The compound according to claim 1, or a pharmaceutically acceptable salt thereof wherein Z is a 6-membered heteroaryl comprising one to three nitrogen atoms, said heteroaryl being optionally substituted by one to three substituents selected from $Y^1$ or $Y^2$.

6. The compound according to claim 1, or a pharmaceutically acceptable salt thereof wherein Z is pyridyl optionally substituted by one to three substituents selected from $Y^1$ or $Y^2$.

7. The compound according to claim 1, or a pharmaceutically acceptable salt thereof wherein Z is pyridyl optionally independently substituted by one or two substituents selected from $Y^1$ and $Y^2$ and wherein said pyridyl is orientated as below:

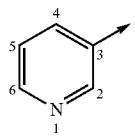

8. The compound according to claim 7 wherein said pyridyl is 6-substituted or 5- and 6-disubstituted.

9. The compound according to claim 1, or a pharmaceutically acceptable salt thereof wherein $Y^1$ and $Y^2$ are each independently selected from:
(i) F;
(ii) Cl;
(iii) CN;
(iv) $(C_1-C_6)$alkyl, optionally substituted by one to six F;
(v) $(C_1-C_8)$alkyloxy, optionally substituted by one to eight F; or (vi) $(C_3-C_6)$cycloalkyl, optionally substituted by one to six F.

10. The compound according to claim 1, or a pharmaceutically acceptable salt thereof wherein $Y^1$ and $Y^2$ are each independently selected from:
(i) F;
(ii) Cl;
(iii) CN;
(iv) $(C_1-C_2)$alkyl, optionally substituted by one to three F; or
(v) $(C_1-C_4)$alkyloxy.

11. The compound according to claim 1, or a pharmaceutically acceptable salt thereof wherein $R^{1a}$ and $R^{1b}$ are each independently selected from $(C_1-C_3)$alkyl; $(C_3-C_5)$cycloalkyl; or, $R^{1a}$ and $R^{1b}$ taken together with the N atom to which they are attached, form a 3- to 6-membered monoheterocycloalkyl, said monoheterocycloalkyl being optionally substituted on a ring carbon atom by one or two F.

12. The compound according to claim 1, or a pharmaceutically acceptable salt thereof wherein $R^{1a}$ and $R^{1b}$ are each independently $(C_1-C_3)$alkyl; or, $R^{1a}$ and $R^{1b}$ taken together with the N atom to which they are attached, form a 3- to 6-membered monoheterocycloalkyl.

13. The compound according to claim 1, or a pharmaceutically acceptable salt thereof wherein $R^2$, $R^3$ and $R^4$ are each independently H, F or Cl.

14. The compound according to claim 1, or a pharmaceutically acceptable salt thereof wherein $R^2$ is F, $R^3$ and $R^4$ are both H; and $R^5$ is F or Cl.

15. A pharmaceutical composition comprising a compound according to claim 1 or a pharmaceutically acceptable salt thereof together with one or more pharmaceutically acceptable excipients.

16. The pharmaceutical composition according to claim 15, wherein said composition further comprises one or more additional therapeutic agents.

17. A method of treating pain, comprising administering to a human or animal in need thereof a therapeutically effective amount of a compound according to claim 1 or a pharmaceutically acceptable salt thereof.

18. The method according to claim 17, wherein said pain is selected from neuropathic, nociceptive or inflammatory pain.

* * * * *